United States Patent
Price, Jr. et al.

(10) Patent No.: US 10,049,772 B1
(45) Date of Patent: Aug. 14, 2018

(54) SYSTEM AND METHOD FOR CREATION, OPERATION AND USE OF A CLINICAL RESEARCH DATABASE

(71) Applicants: LOYOLA UNIVERSITY OF CHICAGO, Chicago, IL (US); LOYOLA UNIVERSITY MEDICAL CENTER, Maywood, IL (US)

(72) Inventors: Ronald N. Price, Jr., Darien, IL (US); Susan Zelisko, Frankfurt, IL (US); Daniel Valdez, Orland Hills, IL (US); Jack Moy, Chicago, IL (US)

(73) Assignees: LOYOLA UNIVERSITY OF CHICAGO, Chicago, IL (US); LOYOLA UNIVERSITY MEDICAL CENTER, Maywood, IL (US)

( * ) Notice: Subject to any disclaimer, the term of this patent is extended or adjusted under 35 U.S.C. 154(b) by 703 days.

(21) Appl. No.: 14/581,743

(22) Filed: Dec. 23, 2014

Related U.S. Application Data

(60) Provisional application No. 62/022,244, filed on Jul. 9, 2014.

(51) Int. Cl.
*G06Q 50/00* (2012.01)
*G16H 50/70* (2018.01)
(Continued)

(52) U.S. Cl.
CPC ......... *G16H 50/70* (2018.01); *G06F 19/322* (2013.01); *G06F 19/3443* (2013.01); *G16H 10/60* (2018.01)

(58) Field of Classification Search
CPC ........ G06Q 50/22; G06Q 50/24; G06Q 40/08; G06Q 10/10; G06F 19/322; G06F 17/30;
(Continued)

(56) References Cited

U.S. PATENT DOCUMENTS 6,502,088 B1 12/2002 Gajda et al.
6,795,825 B2 9/2004 Rishe
(Continued)

OTHER PUBLICATIONS

Cloudera, "Explorys: Improving Healthcare Quality & Costs Using a Big Data Platform", Feb. 20, 2014, 4 pages.

*Primary Examiner* — Tran N Nguyen
(74) *Attorney, Agent, or Firm* — Marshall, Gerstein & Borun LLP

(57) ABSTRACT

In a method, a user at a client device may be provided with a user interface having user interactive controls, including a control to enable selection from among a plurality of disease groups. Each disease group may correspond to a respective set of two or more individual disease codes. A user selection of a disease group of interest may be detected. The set of individual disease codes corresponding to the disease group of interest may be used to identify a set of encounters associated with a patient cohort. The user may be provided with an indication of a number of unique patients in the patient cohort, a number of patients in the cohort having particular characteristic(s), a total number of encounters in the set of encounters associated with the cohort, and/or a number of encounters, in the set of encounters associated with the cohort, having particular encounter characteristic(s).

14 Claims, 23 Drawing Sheets

(51) Int. Cl.
*G06F 19/00* (2018.01)
*G16H 10/60* (2018.01)

(58) Field of Classification Search
CPC ........ G06F 19/30; G06F 19/32; G06F 19/321;
G06F 19/324; G06F 19/325; G06F
19/326; G06F 19/328; G06F 19/34; G06F
19/3418; G06F 19/3456; G06F 19/3462;
G06F 19/3468; G06F 19/3475; G06F
19/3481; G06F 19/36; A61N 1/08; G16H
10/00; G16H 10/20; G16H 10/40; G16H
10/60; G16H 10/65; G16H 15/00; G16H
20/00; G16H 20/10; G16H 20/13; G16H
20/17; G16H 20/30; G16H 20/40; G16H
20/60; G16H 20/70; G16H 20/90; G16H
30/00; G16H 30/20; G16H 30/40; G16H
40/00; G16H 40/20; G16H 40/40; G16H
40/60; G16H 40/63; G16H 40/67; G16H
50/00; G16H 50/20; G16H 50/30; G16H
50/50; G16H 50/70; G16H 50/80; G16H
70/00; G16H 70/20; G16H 70/14; G16H
70/60; G16H 80/00
See application file for complete search history.

(56) References Cited

U.S. PATENT DOCUMENTS

| | | |
|---|---|---|
| 7,567,968 B2 | 7/2009 | Desai et al. |
| 8,447,754 B2 | 5/2013 | Weissman et al. |
| 2013/0197922 A1* | 8/2013 | Vesto .................... G06Q 50/22 |
| | | 705/2 |

* cited by examiner

Clinical Research Database

| 2 | 1,959,776 | 6,581,038 | 16,792,804 | 86,444,904 | 1+Billion |
|---|---|---|---|---|---|
| Institutions | Unique Patients | Patient Encounters | Lab/Rad Procedures | Component Results | Vitals/Phys Findings |

The Program | Data Metrics | Maps | Visualizations | Query Tool | My Queries | Data Request | Data Model | Training/Documentation View Metrics for: ALL INSTITUTIONS (Total) ▼ Year: 2007-2013 ▼

ⓘ Information
☒ Drill to Detail

Encounters by Type

| | |
|---|---|
| Emergency | 283,259 |
| Inpatient | 178,464 |
| Outpatient | 6,119,215 |

IP: 3%
ED: 4%
OP: 93%

Patient data from Jan 2007 - Sep 2013

Top DRGs

| | #Enc | #Pat |
|---|---|---|
| REHABILITATION W CC/MCC | 3,761 | 3,095 |
| NORMAL NEWBORN | 3,241 | 3,228 |
| VAGINAL DELIVERY W/O COMPLICATING DIAGNOSES | 3,074 | 2,783 |
| ESOPHAGITIS, GASTROENT AND MISC DIGEST DISORDERS | 3,000 | 2,645 |
| PERC CARDIOVASC PROC W/O CORONARY ARTERY STENT W/O | 2,315 | 2,072 |
| PERC CARDIOVASC PROC W DRUG-ELUTING STENT W/O MCC | 1,926 | 1,629 |
| BRONCHITIS AND ASTHMA W/O CC/MCC | 1,854 | 1,841 |
| NEONATE W OTHER SIGNIFICANT PROBLEMS | 1,852 | 1,640 |

Top IP Diagnoses (Grouped) +
Top OP Diagnoses (Grouped) +
Top ED Diagnoses (Grouped) +
Top IP Primary Diagnoses Codes +
Top OP Primary Diagnoses Codes +
Top ED Diagnoses Codes +

Top IP Procedures

| | # |
|---|---|
| PACKED CELL TRANSFUSION | 20,831 |
| VENOUS CATH NEC | 15,311 |
| VEIN/ART ENDOTRACHEAL TUBE | 7,839 |
| VENTRAL INFUS NUTRIT SUB | 5,904 |
| CONTINUOS INVASIVE MECHANICAL VENTILATI | 5,834 |
| CORONAR ARTERIOGR-2 CATH | 5,751 |
| ARTERIAL CATHETERIZATION | 5,578 |
| HEMODIALYSIS | 5,230 |
| CV CATH PLCMT W GUIDANCE | 4,825 |
| DX ULTRASOUND-HEART | 4,535 |
| OTHER FETAL MONITORING | 4,508 |
| CONTINUOS INVASIVE | 4,483 |

Top OP Procedures +
Top ED Procedures +
Top Lab Procedures +
Top Lab Components +

FIG. 5A

Clinical Research Database

| 2 Institutions | 1,959,776 Unique Patients | 6,581,038 Patient Encounters | 16,792,804 Lab/Rad Procedures | 86,444,904 Component Results | 1+Billion Vitals/Phys Findings |
|---|---|---|---|---|---|

The Program | Data Metrics | Maps | Visualizations | Query Tool | My Queries | Data Request | Data Model | Training/Documentation View Metrics for: ALL INSTITUTIONS (Total) ▼ Year: 2007-2013 ▼    ⓘ Information  ☒ Drill to Detail

Encounters by Type

Emergency 283,359
Inpatient 178,464
Outpatient 6,119,215

ED: 4%    IP: 3%
OP: 93%

Top DRGs

Top IP Diagnoses (Grouped)    #Enc  #Pat

| | | |
|---|---|---|
| ACUTE MYOCARDIAL INFARCTION (AMI) | 7,866 | 4,472 |
| ACUTE RENAL FAILURE | 17,674 | 11,039 |
| AFIB | 22,166 | 11,967 |
| ANEMIA | 56,026 | 27,330 |
| ANGINA | 74 | 62 |
| ASTHMA | 15,857 | 9,415 |
| ASTHMA EXACERBATION | 4,219 | 2,535 |
| BRONCHITIS | 1,148 | 1,067 |
| BUNDLE BRANCH BLOCK | 13,025 | 7,180 |
| BURN | 3,415 | 2,655 |
| CAD | 75,208 | 18,480 |

Top OP Diagnoses (Grouped) +
Top ED Diagnoses (Grouped) +
Top IP Primary Diagnoses Codes +
Top OP Primary Diagnoses Codes +
Top ED Diagnoses Codes +

Top IP Procedures    #

| | |
|---|---|
| PACKED CELL TRANSFUSION | 20,831 |
| VENOUS CATH NEC | 15,311 |
| VEINSER ENDOTRACHEAL TUBE | 7,839 |
| VENTRAL INFUS NUTRIT SUB | 5,904 |
| CONTINUOS INVASIVE MECHANICAL VENTILATI | 5,834 |
| CORONAR ARTERIOGR-2 CATH | 5,751 |
| ARTERIAL CATHETERIZATION | 5,578 |
| HEMODIALYSIS | 5,230 |
| CV CATH PLCMT W GUIDANCE | 4,825 |
| DX ULTRASOUND-HEART | 4,535 |
| OTHER FETAL MONITORING | 4,508 |
| CONTINUOS INVASIVE | 4,483 |

Top OP Procedures +
Top ED Procedures +
Top Lab Procedures +
Top Lab Components +

Patient data from Jan 2007 - Sep 2013

FIG. 5B

| etrics | Maps | Visualizations | Query Tool | My Queries | Data Request | Data Model | Training/D |

View Metrics for: ALL INSTITUTIONS (Total) ▼  Year: 2007-2013 ▼

Diagnosis Group

The ANEMIA diagnosis group includes the following ICD9 codes:
(Developed by Data Administration based on previous studies. Note: Unless otherwise identified, codes relating to this predefined group are developed locally and are intended for internal use only. Depending on your intended purpose, codes may need to be included or excluded from this group. Please carefully review this group information.)
280 Iron deficiency anemias
280. ICD9 CODE NOT FOUND IN POPULATION DATA
280.0 Iron deficiency anemias secondary to blood loss (chronic)
280.1 Iron deficiency anemias secondary to inadequate dietary iron intake
280.8 Other specified iron deficiency anemias
280.9 Iron (Fe) deficiency anemia
281 ICD9 CODE NOT FOUND IN POPULATION DATA
281.0 Pernicious anemia
281.2 Folate-deficiency anemia
281.3 Other specified megaloblastic anemias not elsewhere classified
282 ICD9 CODE NOT FOUND IN POPULATION DATA
282.0 Hereditary spherocytosis
282.2 Anemias due to disorders of glutathione metabolism
282.5 Sickle-cell trait
282.6 ICD9 CODE NOT FOUND IN POPULATION DATA
283 Acquired hemolytic anemias
283.0 Autoimmune hemolytic anemias
283.1 ICD9 CODE NOT FOUND IN POPULATION DATA
283.2 hemoglobinuna due to hemolysis from external causes
284 ICD9 CODE NOT FOUND IN POPULATION DATA
284.0 ICD9 CODE NOT FOUND IN POPULATION DATA
284.1 Pancytopenia
284.2 Myelophthisis
284.8 Other specified aplastic anemias

CRDB Metrics: IP Diagnoses (Grouped)

Facility: ALL INSTITUTIONS (Total)
Year: All Available

| | ICD9 Code | Description | Encounters | Patients |
|---|---|---|---|---|
| ☒ | multi | ACUTE MYOCARDIAL INFARCTION (AMI) | 7,866 | 4,472 |
| ☒ | multi | ACUTE RENAL FAILURE | 17,674 | 11,038 |
| ☒ | multi | AFIB | 22,166 | 11,967 |
| ☒ | multi | ANEMIA | 56,026 | 27,330 |
| ☒ | multi | ANGINA | 74 | 62 |
| ☒ | multi | ASTHMA | 15,857 | 9,415 |
| ☒ | multi | ATHSMA EXACERBATION | 4,219 | 2,535 |
| ☒ | multi | BRONCHITIS | 1,148 | 1,067 |
| ☒ | multi | BUNDLE BRANCH BLOCK | 13,025 | 7,180 |
| ☒ | multi | BURN | 3,514 | 2,655 |
| ☒ | multi | CAD | 75,208 | 18,480 |
| ☒ | multi | CANCER | 51,389 | 13,106 |
| ☒ | multi | CANCER: BASAL CELL CARCINOMA | 53 | 42 |
| ☒ | multi | CANCER: BLADDER | 2,165 | 821 |
| ☒ | multi | CANCER: BRAIN | 1,487 | 425 |
| ☒ | multi | CANCER: BREAST | 2,990 | 1,353 |
| ☒ | multi | CANCER: CERVICAL | 561 | 273 |
| ☒ | multi | CANCER: COLON | 2,742 | 1,198 |
| ☒ | multi | CANCER: ESOPHAGEAL | 656 | 267 |
| ☒ | multi | CANCER: GASTRIC | 771 | 360 |
| ☒ | multi | CANCER: HEAD AND NECK | 1,469 | 670 |

FIG. 5D

| Top DRGs | | |
|---|---|---|
| Top IP Diagnoses (Grouped) | | |
| Top OP Diagnoses (Grouped) | | |
| Top ED Diagnoses (Grouped) | | |
| Top IP Primary Diagnoses Codes | #Enc | #Pat |
| 401.9 Unspecified essential hypertension | 54,118 | 34,101 |
| 272.4 Other and Unspecified hyperlipidemia | 38,950 | 23,526 |
| 794.31 Nonspecified abnormal electrocardiogram (ECG) | 34,038 | 22,625 |
| V15.82 Personal history of tobacco use, presenting ha | 27,731 | 16,749 |
| 414.01 Coronary atherosclerosis of native coronary ar | 26,883 | 14,656 |
| 250.00 Type II or unspecified diabetes mellitus | 26,789 | 14,999 |
| 530.81 Esophogeal reflux | 25,586 | 16,124 |
| 427.31 Arterial fibrillation | 22,166 | 11,967 |
| 427.89 Other specified cardiac disrhythmias | 21,802 | 16,526 |
| Top OP Primary Diagnoses Codes | | |
| Top ED Diagnoses Codes | | |

FIG. 5F

CRDB Metrics: Inpatient Primary Diagnosis Codes

Facility: ALL INSTITUTIONS (Total)
Year: All Available

| | | | | |
|---|---|---|---|---|
| ☒ | 007.5 | Cyclosporiasis | 4 | 1 |
| ☒ | 008.00 | Intestinal infection due to E coli, unspecifi | 7 | 7 |
| ☒ | 008.03 | Intestinal infection due to enteroinvasive E | 1 | 1 |
| ☒ | 008.09 | Intestinal infection due to other intestinal E | 2 | 2 |
| ☒ | 008.3 | Intestinal infection due to proteus (mirabilis | 3 | 3 |
| ☒ | 008.41 | Intestinal infection due to Staphylococcus | 3 | 3 |
| ☒ | 008.42 | Intestinal infection due to Pseudomonas | 5 | 5 |
| ☒ | 008.43 | Intestinal infection due to canpylobacter | 8 | 7 |
| ☒ | 008.44 | Intestinal infection due to yersinia enterocol | 1 | 1 |
| ☒ | 008.45 | Intestinal infection due to Clostridium diffic | 2,437 | 1,740 |
| ☒ | 008.46 | Intestinal infection due to other anaerobes | 7 | 6 |
| ☒ | 008.47 | Intestinal infection due to other Gram-negativ | 7 | 5 |
| ☒ | 008.49 | Intestinal infection due to other specified ba | 3 | 3 |
| ☒ | 008.5 | Bacterial enteritis, unspecified | 14 | 14 |
| ☒ | 008.61 | Enteritis due to rotavirus | 63 | 60 |
| ☒ | 008.62 | Enteritis due to adenovirus | 2 | 2 |
| ☒ | 008.63 | Enteritis due to Norwalk virus | 2 | 2 |
| ☒ | 008.65 | Enteritis due to calicvirus | 1 | 1 |
| ☒ | 008.67 | Enteritis due to enterovirus not elsewhere cla | 25 | 25 |
| ☒ | 008.69 | Other viral enteritis | 87 | 66 |

FIG. 5G

Top 50 Inpatient Diagnoses by Age Range

460 ⟶

| Unspecified essential hypertension | Esophageal reflux | Tobacco use disorder | Acute kidney failure, unspecified | Anemia, unspecified | Acute posthemorrhagic anemia | Essential hypertension, benign | Unspecified asthma |
|---|---|---|---|---|---|---|---|
| | | Congestive heart failure, unspecified | Depressive disorder, not elsewhere classified | Unspecified constipation | Pure hypercholesterolemia | Hyposmalality and/or hyponatremia | Hypopotassemia |
| Coronary atherosclerosis of native coronary artery | | Long term (current) use of anticoagulants | Dehydration | Obesity, unspecified | Chronic kidney disease, unspecified | Personal history of venous thrombosis and embolism | Pneumonia, organism unspecified |
| Type II or unspecified type diabetes mellitus with | | Unspecified hypothyroidism | Postsurgical perculaneous transluminal coronary an | Unspecified hypertensive kidney disease with chron | Hypotension, unspecified | Outcome of delivery, single liveborn | Need for prophylactic vaccination and inoculation |
| Atrial fibrillation | | | Postsurgical aortocoronary bypass status | Obstructive sleep apnea (adult) (pediatric) | Anxiety state, unspecified | Mitral valve disorders | Hypertrophy of prostate without urinary |
| Other and unspecified hyperlipidemia | | Urinary tract infection, site not specified | Old myocardial infarction | Coronary atherosclerosis of unspecified type of v | Other specified cardiac disrhythmias | Other chronic pulmonary heart diseases | Acute respiratory failure |
| Personal history of tocacco use, presenting hazard | | | | | Transient ischemic attack (TIA), and cerebral infa | Thrombocytopen unspecified | Acidosis |

FIG. 7A

Selection Criteria

Query Description (for futu... Diagnosis Group

Selection Basis ⊕ O Po...

Demographic

Gender* ☐ Male
Age(s) >= [0]
Race* ☐ Asian
☐ Black
☐ Hispa...
☐ Multir...
☐ Other
☐ White 530 — 'No selection in the category indicates 'All'

The ANEMIA diagnosis group includes the following ICD9 codes:
(Developed by Data Administration based on previous studies. Note: Unless otherwise identified, codes relating to this predefined group are developed locally and are intended for internal use only. Depending on your intended purpose, codes may need to be included or excluded from this group. Please carefully review this group information.)

280 Iron deficiency anemias
280. ICD9 CODE NOT FOUND IN POPULATION DATA
280.0 Iron deficiency anemias secondary to blood loss (chronic)
280.1 Iron deficiency anemias secondary to inadequate dietary iron intake
280.8 Other specified iron deficiency anemias
280.9 Iron (Fe) deficiency anemia
281 ICD9 CODE NOT FOUND IN POPULATION DATA
281.0 Pernicious anemia
281.2 Folate-deficiency anemia
281.3 Other specified megaloblastic anemias not elsewhere classified
282 ICD9 CODE NOT FOUND IN POPULATION DATA
282.0 Hereditary spherocytosis
282.2 Anemias due to disorders of glutathione metabolism
282.5 Sickle-cell trait
282.6 ICD9 CODE NOT FOUND IN POPULATION DATA
283 Acquired hemolytic anemias
283.0 Autoimmune hemolytic anemias
283.1 ICD9 CODE NOT FOUND IN POPULATION DATA
283.2 hemoglobinuria due to hemolysis from external causes
284 ICD9 CODE NOT FOUND IN POPULATION DATA
284.0 ICD9 CODE NOT FOUND IN POPULATION DATA
284.1 Pancytopenia
284.2 Myelophthisis
284.8 Other specified aplastic anemias Diagnosis Groups (with impli...

☐ ACUTE MYOCA...
☐ INFARCTION (AM...
☐ ACUTE RENAL...
☐ AFIB
☐ ANEMIA
☐ ANGINA
☐ ASTHMA
☐ ASTHMA EXACERBATION
☐ BRONCHITIS
☐ BUNDLE BRANCH BLOCK

Rehabilitation)
Observation)

...007
...013

...elow...

[Submit]

FIG. 8B

CRDB Queries:

← 540

[Refresh] ← 542

| | | | | | | 544 |
|---|---|---|---|---|---|---|
| | | | | | R Reduce Results | |
| | | | | | A Analyze  O Output | |
| | | | | | E Extract  ⊗ Delete | |
| Job No | Submit Date | Description | Status | Results Saved | Expiration Date | Action |
| 202 | 2014-03-27 17:08:26.0 | Anemia, Females, Age <=50 | Done (12/12) | Yes | 06/25/2014 | R A O E ⊗ |
| 202-1 | 2014-03-27 17:46:04.0 | ...CPT=74000(Rad exam, abdomen, single anteroposterior) | Done (8/8) | Yes | 06/25/2014 | R A O E ⊗ |
| 193 | 2014-03-24 14:44:03.0 | Afib, Age >50, Males, All Years | Done (15/15) | Yes | 06/22/2014 | R A O E ⊗ |
| 193-1 | 2014-03-27 16:40:15.0 | ...CPT=99233 | Done (11/11) | Yes | 06/25/2014 | R A O E ⊗ |
| 193-1-1 | 2014-03-27 17:01:09.0 | ......CPT=93010(ECG, 12-lead) | Done (8/8) | Yes | 06/25/2014 | R A O E ⊗ |
| 183 | 2014-03-18 16:11:35.0 | Pneu(Bl) or Septicemia, 2011-2012 (P) | Done (10/10) | No | | O ⊗ |
| 182 | 2014-03-18 16:03:07.0 | Pneu(Bac) OR Septicemia, 2011-2012, (E) | Done (10/10) | No | | O ⊗ |
| 181 | 2014-03-18 15:48:35.0 | Septicemia, 2011-2012 (Enc-based) | Done (10/10) | No | | O ⊗ |
| 180 | 2014-03-18 15:36:33.0 | Pneu(Bac) > Septicemia, 2011-2012, Pop-based | Done (10/10) | No | | O ⊗ |
| 171 | 2014-03-17 21:38:51.0 | Afib AND DM-T2, 2011, Enc-Based | Done (12/12) | No | | O ⊗ |
| 153 | 2014-03-10 12:50:59.0 | Acute Renal Failure, All Patients, All Sites | Done (12/12) | Yes | 06/08/2014 | R A O E ⊗ |
| 152 | 2014-03-08 18:19:12.0 | Bladder Cancer, All Ages | Done (12/12) | Yes | 06/06/2014 | R A O E ⊗ |
| 150 | 2014-03-07 13:10:35.0 | Afib, All Males > 50 years of age | Done (12/12) | No | | O ⊗ |
| 135 | 2014-02-23 00:22:56.0 | ICD9 402 & 402., All Sites, All Years | Done (12/12) | No | | O ⊗ |
| 132 | 2014-02-23 00:09:45.0 | STEM, IP, All Ages, All Years | Done (12/12) | No | | O ⊗ |
| 126 | 2014-02-19 18:06:21.0 | Diabetes, Age 50-90, All Sexes, Black, Hispanic, CY2012 | Done (12/12) | No | | O ⊗ |
| 107 | 2014-02-10 14:32:30.0 | Viral Pneumonia, CY2013, All Sites | Done (12/12) | Yes | 06/11/2014 | R A O E ⊗ |
| 98 | 2014-02-06 15:37:30.0 | Normal Newborn Delivery, CY2012 | Done (12/12) | No | | O ⊗ |
| 86 | 2014-02-04 10:17:12.0 | AFIB, Males > 50 years of Age | Done (12/12) | No | | O ⊗ |
| 81 | 2014-01-30 20:54:20.0 | All PTs, All classes | Done (12/12) | No | | O ⊗ |

FIG. 9A

| Category | Metric 1 | Metric 2 | Count |
|---|---|---|---|
| Admit:Len of Stay(inpats) | 0-1 Days | | 387 |
| Admit:Len of Stay(inpats) | 2 Days | | 230 |
| Admit:Len of Stay(inpats) | 3 Days | | 207 |
| Admit:Len of Stay(inpats) | 4 Days | | 146 |
| Admit:Len of Stay(inpats) | 5 Days | | 109 |
| Admit:Len of Stay(inpats) | 6 Days | | 124 |
| Admit:Len of Stay(inpats) | 7 Days | | 114 |
| Admit:Len of Stay(inpats) | 8 Days | | 80 |
| Admit:Len of Stay(inpats) | 9 Days | | 61 |
| Admit:Len of Stay(inpats) | 10-19 Days | | 270 |
| Admit:Len of Stay(inpats) | 20-29 Days | | 85 |
| Admit:Len of Stay(inpats) | 30-39 Days | | 24 |
| Admit:Len of Stay(inpats) | 40-49 Days | | 17 |
| Admit:Len of Stay(inpats) | 50-59 Days | | 5 |
| Admit:Len of Stay(inpats) | 60-69 Days | | 2 |
| Admit:Len of Stay(inpats) | 70-79 Days | | 2 |
| Admit:Len of Stay(inpats) | 80-89 Days | | 2 |
| Admit:Len of Stay(inpats) | 90-99 Days | | 1 |
| Admit:Len of Stay(inpats) | 100+ Days | | |
| Admit:Unique Pats from ED | | | 736 |
| Admit:Unique Pats Re-Admi | | | 199 |
| Age Group | 5: 41-50 | | 45 |
| Age Group | 6: 51-60 | | 602 |
| Age Group | 7: 61-70 | | 1,068 |
| Age Group | 8: 71-80 | | 1,040 |
| Age Group | 9: 81-90 | | 755 |
| Age Group | 10: 91-100 | | 84 |
| Age Group | 11: 100+ | | 5 |
| CPT:Unique Patient by CPT | 70450 | CT HEAD/BRN C-MATRL (P-70450) | 249 |
| CPT:Unique Patient by CPT | 71010 | RADEX CH 1 VIEW FRNT (P-71010) | 739 |
| CPT:Unique Patient by CPT | 71020 | RADEX CH 2 VIEWS FRNT&LAT (P-71020) | 445 |
| CPT:Unique Patient by CPT | 71260 | CT THORAX C + MATRL (P-71260) | 115 |
| CPT:Unique Patient by CPT | 74000 | RADEX ABD 1 ANTEROPOST VIEW (P-74000) | 202 |
| CPT:Unique Patient by CPT | 80048 | BASIC METABOLIC PANEL CALCIUM TOTAL (P-80048) | 298 |
| CPT:Unique Patient by CPT | 80053 | COMPRE METAB PANEL (P-80053) | 211 |
| CPT:Unique Patient by CPT | 83735 | MAGNESIUM (P-83735) | 188 |
| CPT:Unique Patient by CPT | 84100 | PHOSPHORUS INORGANIC (P-84100) | 164 |
| CPT:Unique Patient by CPT | 84443 | THYR STIMULATING HORM (P-84443) | 112 |
| CPT:Unique Patient by CPT | 85025 | BLD# COMPL AUTO HHRWP & AUTO DIFFIAL (P-85025) | 206 |
| CPT:Unique Patient by CPT | 85027 | BLD# COMPL AUTO HHRWP (P-85027) | 201 |
| CPT:Unique Patient by CPT | 85610 | PROTHROMBIN TM (P-85610) | 282 |
| CPT:Unique Patient by CPT | 85730 | THROMBOPLASTIN TM PRTL PLSM/WHL BLD (P-85730) | 120 |
| CPT:Unique Patient by CPT | 87641 | IADNA S. AUREUS METHICILLIN RESISTANT AMP PRB TQ (P-87641) | 138 |
| CPT:Unique Patient by CPT | 88305 | LVL IV SURG PATH GROSS&MCRSCP XM (P-88305) | 177 |
| CPT:Unique Patient by CPT | 92960 | CARDIOVERSION ELECTIVE ARRHYT XTRNL (P-92960) | 142 |
| CPT:Unique Patient by CPT | 93005 | ECG-ROUTINE 12 LEAD; TRACING ONLY (P-93005) | 308 |

Job = 193
Submitted By JDOE
Description Afib, Age > 50 Males, All Years
Submit Date 03/24/2014 02:03 PM
Status Done Get the Details of these results

FIG. 9B

| Race | Asian | 37 |
| Race | Black | 239 |
| Race | Hispanic | 10 |
| Race | Other | 124 |
| Race | Preference not indicated | 32 |
| Race | Unknown | 4 |
| Race | White | 3,034 |
| Sex | M | 3,474 |
| Total Encounters | | 13,773 |
| Total Unique Patients w/E | | 3,474 |

← 580

← 584

SELECTION CRITERIA: ← 582
- Facility: ALL
- Selection Basis: ENCOUNTER
- Patient Encounter Dates: 1/2012 - 12/2012
- Patient Class: ALL
- Patient Ages: 50-120
- Patient Sex: M
- Patient Race: ALL
- Account Class: ALL
- Save Results: YES (available through 06/22/2014)
- Diagnosis Group: AFIB 427.31 Atrial fibrillation OR
- ICD9 Codes:

402 Hypertensive heart disease

Notes:
- Clinical data values summarized above are those associated with selected encounters.
- Data reported for "population" searches includes all data for all encounters during the time period specified.
- Users should consult local (e.g., departmental coders) for selections of ICD9 codes that satisfy their search requirements. Codes may vary depending on departmental coding practices.
- Information on Identified Data Issues or Limitations is available under the CRDB 'Documentation' tab.

FIG. 9C

CRDB Query Results Reducer ← 602

Job ID 202.2
Description _____ ← 604
based on job ID 202
Submit Date 2014-03-27 17:08:26.0
Description Anemia, Females, Age <= 50

Reduce by: [CPT Code ▼] ← 606  [Anesthesia ▼] ← 610

☐ 00100 Anesthesia for procedures on salivary glands, including biopsy
☐ 00102 Anesthesia for procedures involving plastic repair of cleft lip
☐ 00103 Anesthesia for constructive procedures of eyelid (eg, blepharoplasty, ptosis surgery)
☐ 00104 Anesthesia for electroconvulsive therapy
☐ 00120 Anesthesia for procedures on external, middle, and inner ear including biopsy, not otherwise specified
☐ 00124 Anesthesia for procedures on external, middle, and inner ear including biopsy, otoscopy
☐ 00126 Anesthesia for procedures on external, middle, and inner ear including biopsy; tympanotomy
☐ 00140 Anesthesia for procedures on eye not otherwise specified
☐ 00142 Anesthesia for procedures on eye, lens surgery
☐ 00144 Anesthesia for procedures on eye, corneal transplant
☐ 00145 Anesthesia for procedures on eye, vitreoretinal surgery
☐ 00147 Anesthesia for procedures on eye, iridectomy
☐ 00148 Anesthesia for procedures on eye, ophthalmoscopy
☐ 00160 Anesthesia for procedures on nose and accessory sinuses; not otherwise specified
☐ 00162 Anesthesia for procedures on nose and accessory sinuses; radical surgery
☐ 00164 Anesthesia for procedures on nose and accessory sinuses; biopsy soft tissue

← 612

*NOTE: For multiple selections, an 'OR' relationship is applied at the encounter level.*

[Submit] ← 614

[Back to My Queries]

Job ID 193-1-1
Description  CPT=93010 (ECG, 12-lead)
Submit Date  2014-03-27 17:01:09.0
based on job ID  197
Submit Date  2014-03-27 16:40:15.0
Description  CPT=99203

Generate additional analysis of the query results:

☐ Account Type
☐ Admit: Length of Stay (Inpatients)
☐ Admit: Unique Patients from ED
☐ Admit: Unique Patients Re-Admitted
☐ Age Statistics
☐ CPT: Unique Encounters by CPT (Top 50)
☐ CPT: Unique Patients by CPT
☐ CPT: Unique Patients by CPT (Top 50)
☐ Dx: Unique Encounters by Dx (Top 50)
☐ Dx: Unique Patients by Dx (Top 50)
☐ Financial Class
☐ Lab Components
☐ Lab Components by Patient Class
☐ Payor Class

[Submit]

FIG. 9E

SYSTEM AND METHOD FOR CREATION, OPERATION AND USE OF A CLINICAL RESEARCH DATABASE

CROSS-REFERENCE TO RELATED APPLICATION

This claims the benefit of U.S. Provisional Patent Application No. 62/022,244, entitled "Methods and Systems for Creating, Operating and Using Clinical Research Databases" and filed on Jul. 9, 2014, the disclosure of which is hereby incorporated herein by reference in its entirety.

FIELD OF THE DISCLOSURE

The present disclosure generally relates to healthcare and, more specifically, to systems and methods for providing clinical analytics for large volumes of data.

BACKGROUND

Over the years, many healthcare technology companies have built clinical data repositories using mainstream relational database technologies, such as those offered by Oracle, Sybase or DB2. These technologies yield data repositories that typically include many thousands of tables representing data relationships and some business logic. Due to the "relational" design of these technologies, pieces of data are forced into highly normalized, relational data models. The enforced relational structure is often optimized for a specific transactional model or logic, and does not lend itself to novel or flexible approaches to data analytics. For example, the relational data structures are not suitable for large-scale storage, or analysis, of unstructured data, such as unstructured textual reports or image files. Moreover, restructuring these data schemas for alternative uses can be time consuming, or simply not feasible, for large, mature relational repositories with trillions of data points. Limitations such as these have become increasingly important as more and more devices in healthcare settings are configured to produce data.

As one example, Structured Query Language (SQL) query builders allow users to join tables and build SQL expressions with complex conditions and logic. Setting up such queries/expressions can be very time consuming and difficult, particularly when the data being analyzed is spread across many different relational database technologies. Moreover, even if a user is trained well enough to construct a syntactically correct SQL expression, the odds that the query will yield precisely the expected/desired cohort of subjects may be low. The complexity of such queries can make it very difficult, for example, to identify a patient cohort by assessing search criteria on a patient-by-patient basis ("population-based" searching) rather than an encounter-by-encounter basis ("encounter-based" searching). Thus, conventional analytics tools using relational database technologies are generally inaccessible to the more casual/untrained user.

Conventional clinical analytics techniques and tools can also require that a user invest a great deal of time and effort up front in order to identify which disease codes (e.g., ICD9 codes) correspond to the desired cohort definition. For example, the user may need to spend hours or days with staff members or other individuals who have special expertise/experience in order to identify the appropriate codes. Once again, this can result in less ease of use, and/or require additional user training.

BRIEF SUMMARY

In one aspect, a computer-implemented method for facilitating patient cohort identification may include providing, by one or more processors, a user at a client device with a user interface including user interactive controls. The user interactive controls may include a control to enable selection from among a plurality of disease groups, and each of the plurality of disease groups may correspond to a respective set of two or more individual disease codes. The method may also include detecting, by one or more processors, a user selection via the user interactive controls of a disease group of interest from among the plurality of disease groups, using, by one or more processors, the respective set of individual disease codes corresponding to the disease group of interest to identify a set of encounters associated with a patient cohort, and providing, by one or more processors, the user an indication of at least one of (i) a number of unique patients in the patient cohort, (ii) a number of patients in the patient cohort having a particular set of one or more patient characteristics, (iii) a total number of encounters in the set of encounters associated with the patient cohort, or (iv) a number of encounters, in the set of encounters associated with the patient cohort, having one or more particular encounter characteristics.

In another aspect, a system for facilitating patient cohort identification may include a web server configured to provide a user at a client device with a user interface including user interactive controls. The user interactive controls may include a control to enable selection from among a plurality of disease groups, and each of the plurality of disease groups may correspond to a respective set of two or more individual disease codes. The web server may also be configured to detect a user selection via the user interactive controls of a disease group of interest from among the plurality of disease groups. The system may also include a server cluster communicatively coupled to the web server and including a plurality of servers. The server cluster may be configured to use the respective set of individual disease codes corresponding to the disease group of interest to identify a set of encounters associated with a patient cohort. The web server may further be configured to cause the user interface to display to the user an indication of at least one of (i) a number of unique patients in the patient cohort, (ii) a number of patients in the patient cohort having a particular set of one or more patient characteristics, (iii) a total number of encounters in the set of encounters associated with the patient cohort, or (iv) a number of encounters, in the set of encounters associated with the patient cohort, having one or more particular encounter characteristics.

In another aspect, a computer-implemented method for facilitating patient cohort identification may include providing, by one or more processors, a user at a client device with a user interface including user interactive controls. The user interactive controls may include (i) one or more controls to enable selection of disease state selection logic, and (ii) a control to enable selection of either a population-based searching algorithm for applying search criteria across multiple encounters on a patient-by-patient basis, or an encounter-based searching algorithm for applying search criteria on an encounter-by-encounter basis. The method may also include detecting, by one or more processors, a user selection via the user interactive controls of (i) disease state selection logic of interest, wherein the disease state selection logic of interest includes a Boolean operator operating on two or more disease states, and (ii) the population-based searching algorithm. The method may also include identifying, by one or more processors, a set of encounters associated with a patient cohort, at least in part by (i) accessing a non-relational database storing patient encounter information for at least a first set of encounters, each encounter of the first set of encounters being associated with a respective one of a first set of patient identifiers, (ii) using the stored patient encounter information to generate a disease code distribution map indicating, for each unique patient identifier in the first set of patient identifiers, one or more respective disease codes associated with the unique patient identifier, (iii) applying the disease state selection logic of interest to the disease code distribution map to determine, for each unique patient identifier, whether the disease state selection logic is satisfied, and (iv) for each unique patient identifier for which the disease state selection logic is satisfied, adding all encounters that are included in the first set of encounters, and associated with the unique patient identifier, to the set of encounters associated with the patient cohort. The method may also include providing, by one or more processors, the user an indication of at least one of (i) a number of unique patients in the patient cohort, (ii) a number of patients in the patient cohort having a particular set of one or more patient characteristics, (iii) a total number of encounters in the set of encounters associated with the patient cohort, or (iv) a number of encounters, in the set of encounters associated with the patient cohort, having one or more particular encounter characteristics.

In another aspect, a system for facilitating patient cohort identification may include a web server configured to provide a user at a client device with a user interface including user interactive controls. The user interactive controls may include (i) one or more controls to enable selection of disease state selection logic, and (ii) a control to enable selection of either a population-based searching algorithm for applying search criteria across multiple encounters on a patient-by-patient basis, or an encounter-based searching algorithm for applying search criteria on an encounter-by-encounter basis. The web server may also be configured to detect a user selection via the user interactive controls of (i) disease state selection logic of interest, wherein the disease state selection logic of interest includes a Boolean operator operating on two or more disease states, and (ii) the population-based searching algorithm. The system may also include a server cluster communicatively coupled to the web server and including a plurality of servers. The server cluster may be configured to identify a set of encounters associated with a patient cohort, at least in part by (i) accessing a non-relational database storing patient encounter information for at least a first set of encounters, each encounter of the first set of encounters being associated with a respective one of a first set of patient identifiers, (ii) using the stored patient encounter information to generate a disease code distribution map indicating, for each unique patient identifier in the first set of patient identifiers, one or more respective disease codes associated with the unique patient identifier, (iii) applying the disease state selection logic of interest to the disease code distribution map to determine, for each unique patient identifier, whether the disease state selection logic is satisfied, and (iv) for each unique patient identifier for which the disease state selection logic is satisfied, adding all encounters that are included in the first set of encounters, and associated with the unique patient identifier, to the set of encounters associated with the patient cohort. The web server may be further configured to cause the user interface to display to the user an indication of at least one of (i) a number of unique patients in the patient cohort, (ii) a number of patients in the patient cohort having a particular set of one or more patient characteristics, (iii) a total number of encounters in the set of encounters associated with the patient cohort, or (iv) a number of encounters, in the set of encounters associated with the patient cohort, having one or more particular encounter characteristics.

BRIEF DESCRIPTION OF THE DRAWINGS

The figures described below depict various aspects of the system and methods disclosed herein. Each figure depicts an embodiment of a particular aspect of the disclosed system and methods, and each of the figures is intended to accord with a possible embodiment thereof.

FIGS. 5A-5G depict example user interface displays corresponding to a data metrics tab of the clinical research database web-based application, according to an embodiment.

FIGS. 7A and 7B depict example user interface displays corresponding to a visualizations tab of the clinical research database web-based application, according to an embodiment.

FIGS. 8A and 8B depict example user interface displays corresponding to a query tool tab of the clinical research database web-based application, according to an embodiment.

FIGS. 9A-9E depict example user interface displays corresponding to a query results tab of the clinical research database web-based application, according to an embodiment.

DETAILED DESCRIPTION

I. Introduction

Figure 1:
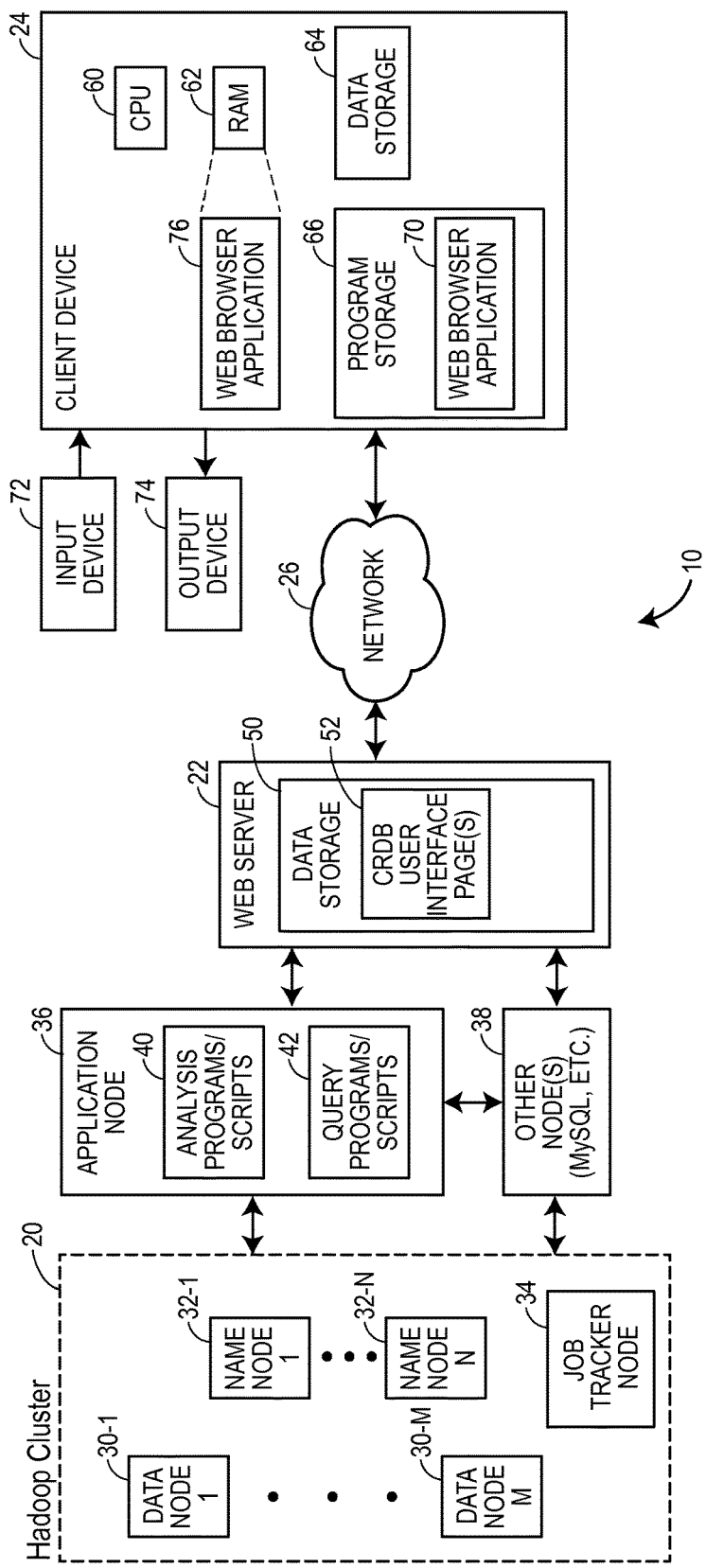
FIG. 1 depicts an example system including components associated with providing users access to a clinical research database, according to an embodiment.

The present embodiments relate to systems and methods associated with the creation, operation and utilization of a clinical research database storing healthcare information (e.g., patient demographic information, encounter type information, lab result information, medication information, diagnosis information, flowsheets, etc.). The clinical research database may utilize a technology platform that supports non-relational data structures. In some embodiments, for example, the clinical research database utilizes a Hadoop platform. By avoiding (or, at least, not requiring) relational data structures, a Hadoop-based system allows rich data structures that are relatively easy to use and understand, and may be able to operate efficiently on virtually any kind of structured or unstructured data in its raw format (e.g., non-standard text data, image data, etc.). In some embodiments, for example, a single Hadoop data model may encapsulate the information contained in many (e.g., hundreds) of different relational tables. Moreover, a Hadoop-based system may be relatively flexible, scalable and/or low cost as compared to relational data repositories, and/or may allow open source tools and techniques to be better leveraged.

By combining rich data structures with the underlying Hadoop technology, very large amounts of data may be more quickly and efficiently processed, new analytic approaches may be enabled, and ease of use may be greatly increased. For example, a wide array of metrics, such as the numbers of diagnoses and/or the number of procedures for various different encounter types (e.g., inpatient, outpatient, emergency, etc.), may be pre-calculated and displayed to users via a web-based application. Moreover, the rich data structures and Hadoop technology may be exploited to provide a simple, intuitive user interface for a query tool of a web-based application. To avoid confusion and reduce user error, for example, the user interface may enforce a "gated" process that guides the user through the steps of building a query while avoiding too much complexity at any one stage. As one example of such a process, the user interface may initially provide controls for only a very limited set of query/search criteria (e.g., several demographic characteristics, several encounter type/date/source characteristics, disease codes with associated AND/OR logic, etc.), and then later allow the user to reduce the result set further in one or more iterations based on additional criteria, and/or allow the user to perform further analysis on the result set.

The use of non-relational data structures may give rise to other benefits as well. Whereas commonly used relational database technologies (e.g., SQL) typically require a great deal of expertise to move between searches that are "encounter-based" (where search criteria are applied across multiple encounters on an encounter-by-encounter basis) and searches that are "population-based" (where search criteria are applied across multiple encounters on a patient-by-patient basis), a Hadoop-based system may, due to fewer and richer data structures, simplify the process of building a query by allowing the user to easily designate whether a search is encounter-based or population-based (e.g., by simply checking a box on a query tool user interface, etc.).

The embodiments described herein may also facilitate cohort identification, and/or the pre-calculation of various metrics, in other ways. For example, individual disease codes, such as International Classification of Diseases, Ninth Revision (ICD9) codes, may be aggregated into various different "disease groups" in advance of a user accessing the web-based application. As just a few examples, an "anemia" disease group may have been defined as a first set of ICD9 codes, an "angina" disease group as a second set of ICD9 codes, an "asthma" disease group as a third set of ICD9 codes, and so on. The web-based application may then display metrics that correspond to some or all of the disease groups (e.g., display the most numerous inpatient diagnoses according to disease group, the total number of encounters in which each disease group was diagnosed, the number of unique patients that were diagnosed at any time as having had each disease group, etc.), and/or allow the user to directly select one or more disease groups as search criteria in the query tool. By pre-defining disease groups in this manner, significant time that is typically spent at the front end of a research project (e.g., considering which ICD9 codes to include as search criteria) may be partially or wholly avoided.

The various approaches described above for making the user interface simpler and more intuitive may provide various benefits. For example, users may be able to build useful queries with little or no training, and even users who have extensive experience with conventional systems may be less likely to generate queries that fail to identify the expected/desired cohort. Various technical improvements may result as well. For example, the non-relational data structures of Hadoop may allow for more efficient processing/consumption of data, thereby preserving processing resources, decreasing power consumption and decreasing processing time. As another example, the distributed processing of a Hadoop-based system may make the clinical research database less vulnerable to outages. As yet another example, aggregating data from numerous different relational databases into a Hadoop cluster, rather than checking all of the relational databases for each query, may allow analyses/queries to be performed with fewer processing cycles and/or fewer network messages, thereby increasing processing efficiency and/or network efficiency.

II. Exemplary System and Environment of an Improved Clinical Research Database

FIG. 1 depicts an example system 10 including components associated with providing users access to a clinical research database, according to an embodiment. The system 10 includes a Hadoop cluster 20, a web server 22 and a client device 24. The Hadoop cluster 20 and/or the web server 22 may be maintained by an institution or entity such as a hospital, a university, a private company, etc., and the client device 24 may be a computing device of an end-user of the clinical research database (e.g., a doctor, a resident, an informatics staff member, etc.). The client device 24 may be communicatively coupled to the web server 22 via a network 26. Network 26 may be a single communication network, or may include multiple communication networks of one or more types (e.g., one or more wired and/or wireless local area networks (LANs), and/or one or more wired and/or wireless wide area networks (WANs) such as the Internet).

The Hadoop cluster 20 may include a number of servers for storing the information of the clinical research database, and for performing various processing operations with respect to that data. In the embodiment of FIG. 1, for example, the Hadoop cluster 20 includes M data nodes 30-1 through 30-M (M being any integer greater than or equal to one, such as six, eight, etc.), N name nodes 32-1 through 32-N (N being any integer greater than or equal to one, such as one, two, etc.) and a job tracker node 34. Each of the nodes may represent a distinct physical server device, or some or all of the nodes may be combined on a single physical server, in various different embodiments. Moreover, the nodes may be physically/geographically in one location, or distributed and communicatively coupled by one or more LANs and/or WANs. Generally, data nodes 30-1 through 30-M may store the clinical research database information (e.g., patient encounter information), name nodes 32-1 through 32-N may manage a virtual file system of the Hadoop cluster 20, and job tracker node 34 may distribute tasks (e.g., MapReduce tasks) to specific other nodes in the Hadoop cluster 20.

The Hadoop cluster 20 may implement a Hadoop framework, such as Apache Hadoop, and may support a Hadoop distributed file system (HDFS) that splits files into blocks distributed among the data nodes 30-1 through 30-M. The stored data may correspond to any of one or more non-relational, complex, Hive-supported data types, such as structures, arrays, structures of arrays and/or arrays of structures. The data may include patient demographic information (e.g., age, gender, race/ethnicity, etc.), encounter type information (e.g., inpatient, outpatient, emergency, etc.), lab result information, medication information, diagnosis information, surgical procedure information and/or flowsheets, for example, and may include data collected from one or more medical centers, hospitals and/or other institutions (e.g., data converted from electronic medical record (EMR) systems of those institutions, as discussed below in Section III). Some more specific examples of data models that may, in some embodiments, be used for data stored in data nodes 30-1 through 30-M are provided below in Section IV.

The example system 10 may also include an application node 36 and one or more other nodes 38. The application node 36, and one, some or all of the other node(s) 38, may be coupled to the Hadoop cluster 20, and to each other, via one or more LANs and/or WANs, and/or via one or more direct cable connections in a rack, for example. The application node 36 may implement various types of middleware, such as analysis programs/scripts 40 that may be used to generate patient and/or encounter metrics using the information stored in data nodes 30-1 through 30-M, and query programs/scripts 42 that may be used to perform user query operations using the information stored in data nodes 30-1 through 30-M. Generating metrics and performing queries will be discussed in further detail below. The other node(s) 38 may include one or more additional nodes needed for operation of the Hadoop cluster 20 and/or for operations external to the Hadoop cluster 20. The application node 36 may submit jobs to the Hadoop cluster 20, receive results from the Hadoop cluster 20, and parse and upload the results to a MySQL database included in other node(s) 38, for example. One or more types of processes on the Hadoop cluster 20 may also upload and/or download data directly to and/or from a MySQL database in other node(s) 38.

The web server 22 may be coupled to the application node 36 and/or one or more of the other node(s) 38 via one or more LANs and/or WANs, and/or via one or more direct cable connections in a rack, for example. The web server 22 includes a data storage 50, which may be a persistent memory storing one or more user interface web pages 52 for a web-based application that allows users to access/use the clinical research database. The user interface web page(s) 52 may include HyperText Markup Language (HTML) instructions, JavaScript instructions, JavaServer Pages (JSP) instructions, and/or any other type of instructions suitable for defining the content and presentation of the web page(s) 52.

While many users and client devices may access web page(s) 52 and use the clinical research database, for clarity FIG. 1 illustrates only the example client device 24 of a single user. Client device 24 may be a personal computer (e.g., desktop, laptop, notebook), or any other suitable stationary or portable computing device, such as a tablet or smartphone, for example. As illustrated in FIG. 1, client device 24 may include a central processing unit (CPU) 60 to execute computer-readable instructions, a RAM 62 to store the instructions and data during operation of programs, a data storage 64 that may include persistent memory to store data used by the programs executed by CPU 60, and a program storage 66 that may include persistent memory to store the programs/instructions executed by CPU 60, including, for example, a web browser application 70. By way of example, the data storage 64 and/or the program storage 66 may be implemented on a hard disk drive coupled to CPU 60 via a bus (not shown in FIG. 1). More generally, the components 60, 62, 64 and 66 may be implemented in any suitable manner according to known techniques. While client device 24 in the example of FIG. 1 includes both storage and processing components, client device 24 may instead be a so-called "thin" client that depends upon another computing device for certain computing and/or storage functions. For example, data storage 64 and/or program storage 66 may be external to client device 24 and connected to client device 24 via a network link.

Further, client device 24 may be coupled to an input device 72 that allows the user to enter inputs to client device 24, and an output device 74 that allows the user to view outputs/displays generated by client device 24. The input device 72 may be a pointing device such as a mouse, keyboard, trackball device, digitizing tablet or microphone, for example. The output device 74 may be a display monitor, for example. In one embodiment, input device 72 and output device 74 may be integrated as parts of a single device (e.g., a touch screen device). Using the input device 72 and the output device 74, a user may be able to interact with graphical user interfaces (GUIs) provided by the web browser application 70 of client device 24.

When CPU 60 executes the web browser application 70, RAM 62 may temporarily store the instructions and data required for its execution. In FIG. 1, the web browser application 70 being executed is represented in the program space of RAM 62 as web browser application 76. When the user uses the web browser application 76 to access one of the web page(s) 52, for example, the page may be stored as a local copy (not shown in FIG. 1) in RAM 62, and the web browser application 76 may interpret the instructions of the local copy to present the page to the user and allow the user to interact with the page.

In operation, a user using client device 24 may use the web browser application 76 to access, via network 26 (e.g., the Internet), web page(s) 52 of the web server 22. By providing informational displays and interactive controls, the web page(s) 52 may enable the user to view various metrics relating to the data stored in data nodes 30-1 through 30-M, and/or to perform queries on that data. An example set of user interface displays provided by web page(s) 52 is provided in FIGS. 4-9 (discussed below in Section V), according to one embodiment. When the web server 22 receives a query from client device 24, the query parameters may be passed to the application node 36. The application node 36 may then submit a corresponding query job to the Hadoop cluster 20, and receive the query results from the Hadoop cluster 20. The application node 36 may also perform one or more other operations, such as parsing the query results and uploading the parsed results to a MySQL database included in other node(s) 38, for example. The application node 36, and/or one or more of other node(s) 38, may return the results to web server 22 for display to the user of client device 24 via web page(s) 52.

In an alternative embodiment, the user may access the clinical research database using a downloaded software component (e.g., a software component that is downloaded and stored in program storage 66) rather than a web page accessed via web browser application 76. For example, client device 24 may be a smartphone of the user, and program storage 66 may store a smart phone application that was previously downloaded from web server 22 (or another server) via network 26. For example, the application may generate the user interface displays discussed below in connection with FIGS. 4-9, and may communicate with the application node 36 or another server in Hadoop cluster 20 (e.g., to submit queries and get query results) via network 26.

Figure 2:
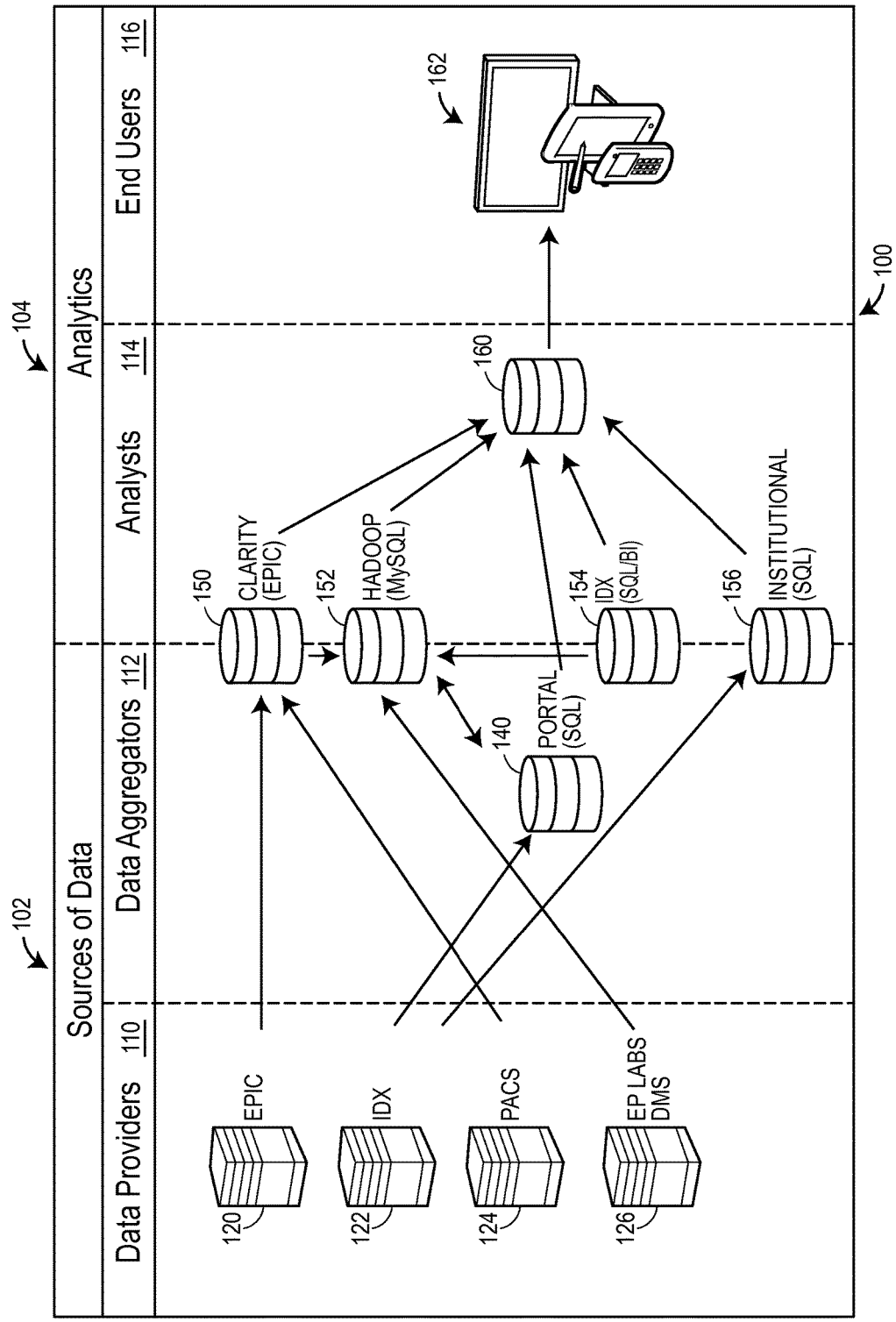
FIG. 2 depicts an example environment in which the system of FIG. 1 may be utilized, according to an embodiment.

FIG. 2 depicts an example environment 100 in which the system 10 of FIG. 1 may be utilized, according to an embodiment. In the environment 100, a number of data sources 102 are used to provide data that may be analyzed using a number of analytics tools 104. The data sources 102 may include data providers 110 as well as data aggregators 112, and the analytics tools 104 may include data analysts 114 as well as end user tools 116. In the example embodiment of FIG. 2, the data providers 110 include an EPIC data source 120 for providing EMR data, an IDX data source 122 for providing Current Procedural Terminology (CPT) codes and ICD9 codes relating to services provided by physicians, a picture archiving and communication system (PACS) data source 124 for providing medical images, and an electrophysiology (EP) labs data management system (DMS) data source 126 for providing electrophysiology test results. PORTAL 140 is an application delivery framework that may aggregate data from IDX data source 122 and/or other sources to implement intranet applications.

Some systems within the environment 100 may incorporate both data aggregator functionality and analytic functionality. For example, a Clarity system 150 may aggregate data from EPIC data source 120 and PACS data source 124 and provide analytic tools for that data, an IDX system 154 may aggregate data from IDX data source 122 and provide analytic tools for that data, and an institutional system 156 may aggregate data from IDX data source 122, and/or one or more other sources, and provide analytic tools for that data.

A Hadoop system 152 (e.g., Hadoop cluster 20 of FIG. 1) may aggregate data from some of the data providers 110 directly, or indirectly via other data aggregators 112 and/or data analysts 114. For example, Hadoop system 152 may aggregate data directly from the EP labs DMS data source 126, but aggregate data from EPIC data source 120 and PACS data source 124 via the Clarity system 150, and aggregate data from IDX data source 122 via PORTAL 140.

The Hadoop system 152, and/or one or more other of the systems with analytic capabilities, may provide analysis results/outputs to a distribution service 160. In the embodiment of FIG. 2, for example, the distribution service 160 also receives results/outputs from the Clarity system 150 and the institutional system 156. The distribution service 160 may be provided by a program stored in program storage 66 and executed by CPU 60 of client device 24 in FIG. 1, or by a program executed by a server remote from client device 24 (e.g., in web server 22), for example. The distribution service 160 may collect the outputs/results for presentation to a user's computing device 162 (e.g., client device 24 of FIG. 1). When presenting outputs (e.g., metrics and/or query results) from the Hadoop system 152, for example, an output device of the computing device 162 (e.g., output device 74 of FIG. 1) may present the user with one or more of the displays that are shown in FIGS. 4-9 and discussed below in Section IV. In some embodiments, the distribution service instead, or also, is configured to enable one or more other analytic systems to access the clinical research database automatically/programmatically for direct use as a data source. For example, a separate application may utilize an application programming interface of the distribution service 160 to submit a query and obtain query results, without the need for any user interface displays.

Each of the data providers 110, data aggregators 112 and/or data analysts 114 may be a dedicated physical server or group of servers. Alternatively, some servers or server groups may combine the functionality and/or data storage of two or more of the data providers 110, data aggregators 112 and/or data analysts 114. In other embodiments, the Hadoop system 152 may be situated in an environment different than the environment 100 of FIG. 2, and/or the different aggregators 112 may collect data from more, fewer and/or different data providers 110 (and/or more, fewer and/or different other data aggregators 114) than shown in FIG. 2. As just one example, instead of (or in addition to) aggregating EPIC EMR data, the Hadoop system 152 may aggregate data from a Cerner EMR system.

III. Exemplary Creation of an Improved Clinical Research Database

Figure 3:
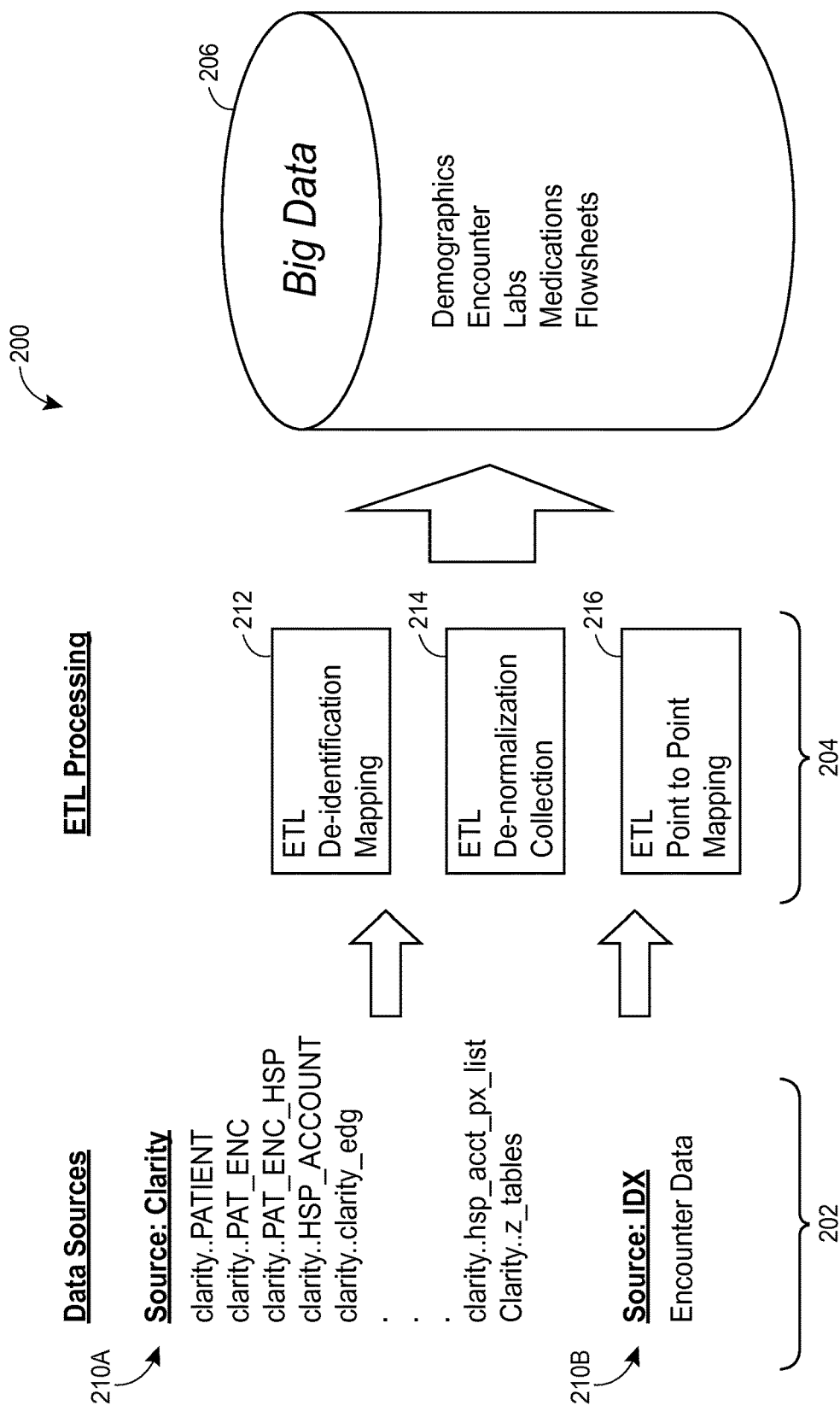
FIG. 3 depicts an example extract-transform-load (ETL) process, according to an embodiment.

FIG. 3 depicts an example extract-transform-load (ETL) process 200, according to an embodiment, which may be used to create a de-identified (anonymous), de-normalized (non-relational) dataset that can be stored and processed in the Hadoop cluster 20 of FIG. 1. In particular, the ETL process 200 may convert data from data sources 202, using ETL processing programs 204, in order to generate a "big data" repository 206 (i.e., the data of the clinical research database). In the example shown in FIG. 3, the data sources 202 include an institution's Clarity relational data warehouse (i.e., an EPIC EMR data reporting repository of the institution) and an IDX repository of physician billing data. In other embodiments and/or scenarios, however, the data sources 202 may include additional, fewer and/or different data sources as compared to those shown in FIG. 3, such as one or more sources of EMR data other than EPIC/Clarity, and/or one, some or all of the other data providers 110 and/or data aggregators 112 shown in FIG. 2, for example.

The ETL processing programs 204 may include programs that extract data from the data sources 202 and transform the extracted data into a series of files in a different, non-relational data structure that is suitable for storage and processing in Hadoop. For example, the ETL programs 204 may include programs that provide de-identification mapping 212 to anonymize data, de-normalization/collection 214 to collect data from the relational data structures and transform the data to one or more non-relational, Hadoop/Hive data models, and point-to-point mapping 216 to transfer certain data elements without any transformation (e.g., to transfer a provider name or a patient name, having a string data type, to the data repository 206 without first transforming the provider or patient name to a code having an integer data type, etc.). The resulting non-relational data structures may be complex data types in Hive, for example, such as arrays, structures, arrays of structures and/or structures of arrays. To provide a more specific example, one complex data type in Hive may be an admission diagnosis array of structures ("admit_dx"), with the structures in the array including the diagnosed ICD9 code ("icd9_code"), a description of the diagnosed ICD9 code ("icd9_dx_desc"), and unstructured text notes associated with the diagnosis ("icd9_free_text"). Some specific examples of Hadoop data models are discussed further below, in Section IV.

Once the data from data sources 202 has been extracted and transformed, the ETL programs 204 may load the data into the repository 206. Depending on the data sources 202, the repository 206 may include many different types of healthcare-related data, such as patient demographic information, encounter information, labs data, medication information, flowsheets, etc., and may be utilized by the system 10 of FIG. 1 to generate metrics, perform queries, etc., as discussed herein. In various embodiments and/or scenarios, the ETL programs 204 may extract, transform and load all source data at an initial stage before the system 10 is put to use, and/or may operate in an ongoing manner as data continues to be generated and made available by the data sources 202.

IV. Exemplary Hadoop Data Models

The non-relational nature of Hadoop allows great flexibility in the form in which data is stored. Data may be stored as "streams," for example, with delimiters (e.g., carats ("^"), tildas ("~"), pipes ("|")) denoting the different fields within a data stream, and with any type of simple or complex data structures included in the data stream. In this manner, a single data model may encapsulate the information from many (e.g., tens, hundreds, etc.) of relational tables. Moreover, the data in the data stream may include unstructured data, such as unstructured text reports, image data, binary large objects (BLOBs), etc.

As discussed above, the ETL process 200 of FIG. 3 may convert data to data models that can be stored and processed by the Hadoop system. In one embodiment, the resulting set of data models includes at least a patient demographics model, a patient encounters model, a labs data model, a flowsheet data model, a medication list model, and an encounter payor data model. For example, the data models may be structured as follows (with the text following each field being included here solely for descriptive purposes):

a) Patient Demographics (de-identified)
1. State Identifier (Code)—Patient's state identifier, as a coded value.
2. State (Abbr)—Patient's state, as a descriptive string.
3. Gender—Patient's gender.
4. Year of Birth—The patient's year of birth.
5. Race Identifier—Patient's race identifier(s) (can contain more than one identifier).
6. Ethnic Identifier (Code)—Patient's ethnic identifier, as a coded value.
7. Ethnic Identifier—Patient's ethnic identifier, as a text description.
8. Date of Death—Date of patient's death.
9. Facility Name—Submitting facility name.
10. Service Area Identifier—Service area identifier.

b) Patient Encounters
1. Encounter Start Date/Time—Encounter start date and time.
2. Encounter Stop Date/Time—Encounter stop date and time.
3. Age At Encounter—Patient age at time of encounter.
4. Age At Discharge—Patient age at time of discharge.
5. Encounter Class (Code)—Encounter class, as a coded value.
6. Encounter Class (Text)—Encounter type, as a text description.
7. Encounter Type (Code)—Encounter type, as a coded value.
8. Encounter Type (Text)—Encounter type, as a text description.
9. Admitting Dept (Code)—Admitting department, as a coded value.
10. Admitting Dept (Abbr)—Admitting (or Encounter) department abbreviation.
11. Discharge Dept (Code)—Encounter discharge department's coded value.
12. Discharge Dept (Abbr)—Encounter discharge department's abbreviation.
13. Admitting Provider ID (Code)—Admitting physician as a coded value.
14. Admitting Provider Name—Name of the admitting provider.
15. Attending Provider ID (Code)—Attending provider ID, as a coded value.
16. Attending Provide Name (Text)—Attending provider name, as a descriptive string value.
17. Attending List—A coded list of all attendings that saw a patient during an admission.
    Attending Provider ID—Attending Provider ID, as a coded value.
    Provider Name—Attending as a descriptive name.
    Provider Start Date—Provider service start date.
    Provider End Date—Provider service end date.
18. Encounter Disposition (Code)—Encounter disposition, as a coded value.
19. Encounter Discharge Disposition—Encounter discharge disposition.
20. Admitting Diagnosis—Admitting diagnosis.
    Admitting DX Code—Admitting DX code, as an ICD9 code.
    Admitting DX Description—Admitting DX description.
    Admitting DX (free text) Entry—Admitting DX free-text entry.
21. Primary Encounter Diagnosis—Encounter primary diagnosis.
    Primary Admitting DX Code—Primary admitting diagnosis code, as an ICD9 code.
    Primary Admitting DX Code Description—Primary admitting DX code, as a text description.
22. Diagnoses List (Code)—Encounter's diagnoses, as coded values.
    DX List—ICD9 codes associated with an encounter, as coded values.
    DX List Description—ICD9 associated with an encounter, as a string value.
23. CPT List—In-patient—List of all CPTs associated with in-patient encounter. Source is billing data.
    In-Patient CPT List—List of all CPT codes associated with an in-patient encounter, as coded ICD9 values.
    CPT Dates—Dates associated with a list of in-patient CPT codes.
    CPT Provider ID—Provider IDs associated with a captured list of in-patient CPT codes.
    CPT Provider Name—Provider names associated with a list of captured in-patient CPT codes.
24. Procedure Lists—List of procedures associated with an encounter.
    Procedure Number (Code)—List of numeric procedure identifiers coded as a string.
    Procedure Description (Text)—List of procedure names as descriptive text.
    Procedure Date/Time—List of procedure date and times.
    Procedure Provider ID—List of provider IDs that performed captured procedures.
    Procedure Provider Name—Descriptive name of the provider that performed the procedure.
25. DRG List—Encounter's billed MS DRG listing.
    DRG Internal ID (Code)—Internal DRG identifier associated with the encounter.
    DRG Number (Code)—List of DRG codes associated with an encounter.
    DRG Name (Text)—List of DRGs associated with the encounter, as a descriptive text.
26. Diagnoses List (MD billing)—Physician diagnosis listing.
    MD CPT ICD9 Code—ICD9 codes associated with CPTs that are captured from MD billing.

MD CPT ICD9 Description—ICD9 codes that are associated with CPT codes that are captured through MD billing.
27. CPT List (MD billing)—Physician CPT listing.
   MD CPT List (Code)—List of MD CPT codes associated with an encounter.
   MD CPT Date/Time—Date and times associated with MD CPT codes.
   MD CPT Provider ID (Code)—Provider IDs associated with MD billing codes.
   MD CPT Provider Names—Provider names associated with MD CPT billing codes.
28. Associated Visit List—List of associated encounters.
   Associated Visit Date/Times—Associated visit date and times.
   Associated Visit Status (Code)—Associated visit status, as a coded value.
   Associated Visit Status (Text)—Associated visit status, as a descriptive text.
   Associated Visit Type (Code)—Associated visit type, as a coded value.
   Associated Visit Type (Text)—Associated visit type, as descriptive text.
   Associated Visit Provider ID (Code)—Associated visit provider ID, as coded value.
   Associated Visit Provider Name—Associated visit provider name, as text.
   Associated Visit Dept ID (Code)—The department associated with encounter coded, as an integer value.
   Associated Visit Dept Name (Text)—The department associated with encounter coded, as a string value.
29. Service Area ID (Code)—Service area identifier as a coded value.
30. Facility Name (Text)—Encounter location.
31. In-Patient Re-Admission Flag (Code)—Re-admission flag, as a coded value.
32. In-Patient Re-Admission Date—In-patient re-admission date.
33. In-patient Re-admission Locator—In-Patient re-admission locator flag.
34. In-Patient Re-admission Days—In-patient re-admission days.
35. In-Patient Re-Admission DX (Code)—In-patient re-admission diagnosis, as an ICD9 coded value.
   In-Patient Re-Admission DX List (Code)—List ICD9 codes associated with a re-admission, as coded values.
   icd9_dx_desc—ICD9 associated with a re-admission, as a string value.
36. Combo DX List—A combined list of all diagnoses (ICD9 codes) from all sources associated with this encounter.
37. Combo CPT List—A combined list of all CPT codes from all sources associated with this encounter.
38. In Emergency Department—Indicates whether patient was in the emergency department.
39. Arrival Type (Code)—Patient arrival type, as a coded value.
40. Arrival Type Description (Text)—Patient arrival type, as a text description.
41. Transferred From (Code)—Transferred from, as a coded value.
42. Transferred From Name (Text)—Transferred from, as a descriptive string name.
43. Social History—Social history factors associated with an encounter.
   Tobacco User—Tobacco user.
   Cigarette Smoker—Cigarette smoker.
   Cigar Smoker—Cigar smoker.
   Chewing Tobacco User—Chewing tobacco user.
   Alcohol User—Alcohol user.
   Alcohol Source—Alcohol source.

c) Lab Data
1. Order Date—Date of lab order.
2. Time Taken—Time that the lab test/specimen was taken.
3. Result Date—Date of lab result.
4. Procedure Code—Laboratory procedure, as a coded value.
5. Procedure Description—Laboratory procedure description.
6. CPT Code—CPT code associated with this lab.
7. Component ID—Lab component identifier, as a coded value.
8. Component Abbreviation (Abbr)—Lab component abbreviation.
9. Component Name—Descriptive name of the lab component.
10. Result Value—Lab result value.
11. Result Flag Code—Result flag, as a coded value.
12. Result Flag Description (Text)—Result flag description.
13. Reference Low Indicator—Reference low indicator or low range.
14. Reference High Indicator—Reference high indicator or high range.
15. Reference Unit—Reference units.
16. Component Comment—Lab component comment.
17. Abnormal Flag—Flag indicating whether lab result is abnormal.
18. Authorization Provider ID—Coded identifier of the authorizing provider.
19. Authorization Provide Name—Authorizing provider name, as a descriptive string value.
20. Lab Report (Text)—The textual report of the lab test.
21. Service Area ID—Service area ID, as a coded value.
22. Facility Name (Text)—Location of the encounter.

d) Flowsheet Data
1. Record Type—Coded value to identify a Concept or Flowsheet record.
2. Template Name—Name of template on which flowsheet information was entered.
3. Flowsheet Measure Name—Name of measure within a flowsheet.
4. Flowsheet Measure Display—Name which is displayed for this specific flowsheet measure.
5. Flowsheet Type—Type of data entered for a specific flowsheet (e.g., Text, Date)
6. Recorded Time—Time the flowsheet/concept was recorded.
7. Measured Value—Value entered for specific flowsheet measure.
8. Display Value—Value which is displayed for users for that specific flowsheet measure.
9. Measurement Comment (Text)—Comment that was entered for this measure.
10. Taken Username—Name of the user taking the measure.
11. Concept Name—Concept name.
12. Concept Abbreviation—Abbreviation for concept being entered.
13. Concept Value—Value entered for specific concept.

14. Concept Display—Information/Name displayed for this concept.
15. Concept Source—Name of form/screen concept information was pulled from.
16. Entered Username—Username for the person who entered the flowsheet/concept.

e) Medication List
1. Medication ID—Medication ID listed for this specific medication.
2. Verified—Indicates whether the medication was verified by a pharmacist.
3. Non-verified Info—Information as to why medication was not verified.
4. Scheduled Time—Time medication was scheduled to be taken.
5. Medication Name—Name of medication given.
6. Time Taken—Time medication was taken.
7. Due Description—Description of medication due code.
8. Result Description—Description of result of medication being dispensed.
9. Reason Description—Description of reason why medication was not given.
10. Epic Username—Name of the user that took action on the administration.
11. Saved Time—Time the medication administration information was saved in system.
12. SIG—Patient instructions for medication.
13. Display Quantity Unit Description—Quantity Unit Description which is displayed to user.
14. Medication Comments—Comments associated with the medication order/administration.
15. Admitting Provider ID—Admitting provider, as a coded value.
16. Provider Name—Name of admitting provider.
17. Department ID—Department identifier, as a coded value.
18. Department Name—Name of department medication was ordered/administered.
19. Patient Age—Patient age at time medication was given.
20. Order Time—Time medication was ordered.
21. Verification Time—Time medication was verified.
22. Dispense Time—Time medication was dispensed.
23. Display Name—The name of the medication as it appears on the medication record itself.
24. Dose Info—Discrete dose given for medication.
25. Dose Unit Info—Abbreviation for unit of medication dose.
26. Discrete Dose—Combination of dose and unit for medication.
27. Ordering User—Name of the user who ordered the medication.
28. Service Description—Description of the service who ordered the medication.
29. Medication Route Description—Description of route medication was administered
30. Order Status—Description of medication order status.
31. Service Area Name—Location name where medication was ordered/administered.

f) Encounter Payor Data
1. Primary Payor ID (Code)—Primary payor ID, as a coded value.
2. Primary Payor Name (Text)—Primary payor name, as descriptive text.
3. Financial Class (Code)—Financial class, as a coded value.
4. Financial Class (Text)—Financial class, as descriptive text.
5. Plan ID (Code)—Payer plan, as a coded value.

It is understood that, in other embodiments, different types of data models, more or fewer than six data models, and/or data models with different numbers and/or types of fields may be utilized instead of the example data models shown above.

V. Exemplary Web-Based Application for Using an Improved Clinical Research Database FIGS. 4-9 depict example user interface displays provided to a user by a web-based application, according to an embodiment. The web-based application may be accessed via an internal website of an institution (e.g., via PORTAL 140 of FIG. 2), for example. FIGS. 4-9 depict the user interface displays as they might appear within a display of a web browser, for example. A user may provide inputs to (e.g., activate/select controls of) the user interface displays by actions such as keyboard entries, mouse and/or touchpad clicks and movement, touch (e.g., if the user accesses the displays using a smartphone, tablet, etc.) and/or other input means. With reference to the embodiment shown in FIG. 1, the web server 22 may make one or more of web page(s) 52 available to web browser application 76 of client device 24. The web browser application 76 may then cause the output device 74 to display some or all of the screens of FIGS. 4-9 to the user, and may cause the CPU 60 to recognize and act upon user inputs (made with input device 72) according to the functionality described below.

Figure 4:
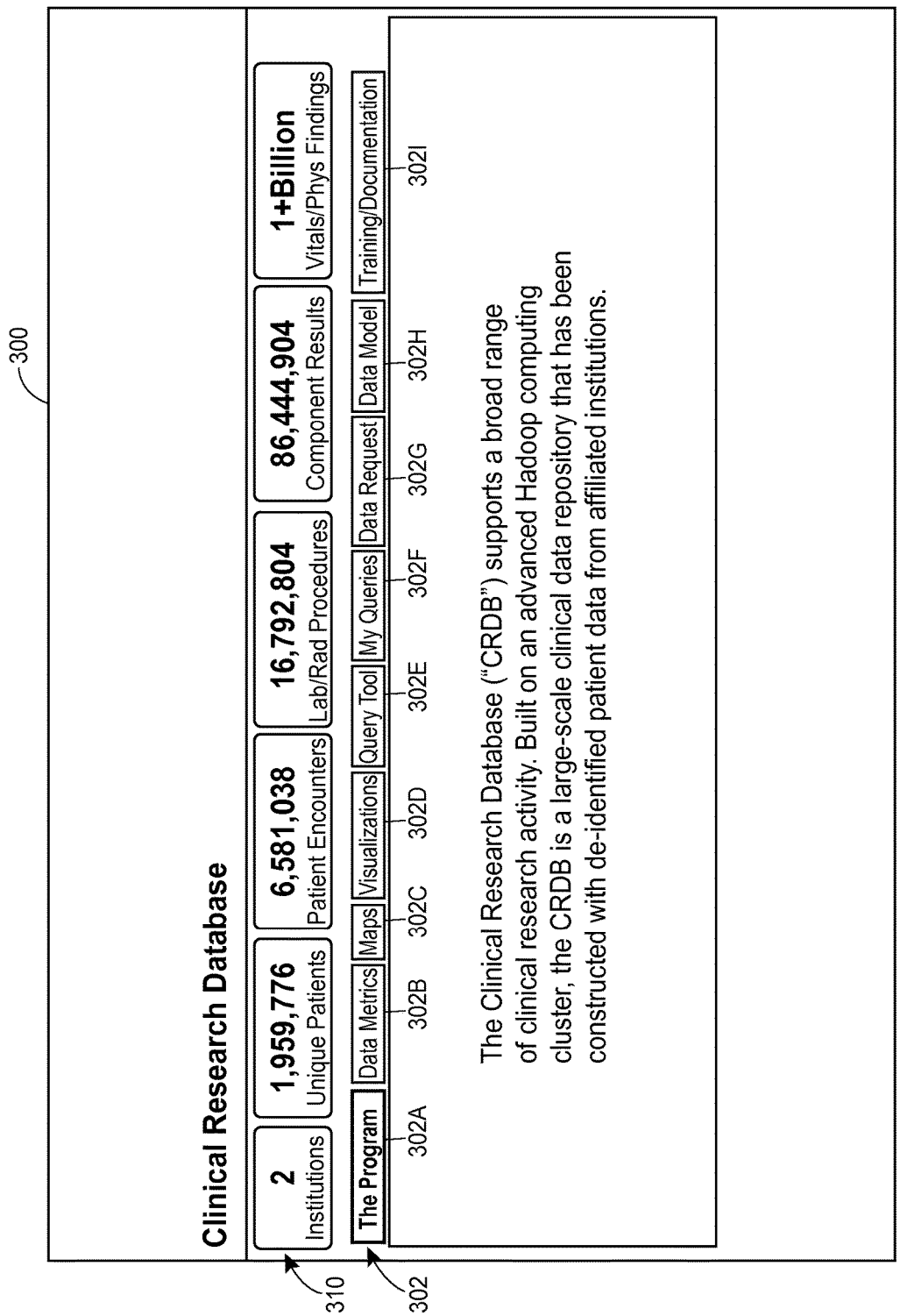
FIG. 4 depicts an example user interface display corresponding to a default tab of a clinical research database web-based application, according to an embodiment.

Referring first to FIG. 4, a user interface display 300 corresponds to a default/home tab 302A of the web-based application (i.e., the tab labeled "The Program"), according to an embodiment. The display 300 may include text providing a high-level introduction to the clinical research database, for example. The display 300 may also include a number of different tabs 302 (including the default/home tab 302A), which may correspond to various different tools, information sources and/or references/links, for example. Specifically, in the example embodiment of FIGS. 4-9, the tabs 302 include the default/home ("The Program") tab 302A, a data metrics tab 302B, a maps tab 302C, a visualizations tab 302D, a query tool tab 302E, a stored query ("My Queries") tab 302F, a data request tab 302G, a data model tab 302H and a training/documentation tab 302I. The display 300 may appear as a starting/default screen when a user first accesses the web-based application. After the user navigates away from the display 300 by selecting (e.g., clicking on) one of tabs 302B through 302I, the user may return to the display 300 by selecting the default/home tab 302A. It is understood that, in other embodiments, the display 300 may include more tabs, fewer tabs and/or tabs having different functionality than those shown in FIGS. 4-9, and/or may allow the user to navigate between screens and/or functions using a mechanism other than tabs (e.g., drop down menu options, etc.).

In addition to the tabs 302, the display 300 may include a number of predetermined metrics 310. The metrics 310 may have been pre-calculated by processing the data stored in the Hadoop system using scripts and/or programs running on an application server (e.g., analysis programs/scripts 40 running on application node 36 of FIG. 1), for example. In the embodiment of FIG. 4, the metrics 310 include the number of institutions that sourced the data stored in the clinical research database, the number of unique patients reflected in the clinical research database, the number of patient encounters reflected in the clinical research database, the number of lab and radiology procedures reflected in the clinical research database, the number of component results reflected in the clinical research database, and the number of vitals/physician findings reflected in the clinical research database. In other embodiments and/or scenarios, however, the metrics 310 may include more, fewer and/or different metrics than those shown in FIG. 4, or the display 300 may not show the metrics 310.

If the user selects the data metrics tab 302B, the web-based application may cause the client device to present the user interactive display 320 to the user, as seen in FIG. 5A. The display 320 may again show the metrics 310, along with additional pre-calculated metrics 322, 324 and 326. In the example embodiment of FIG. 5A, the metrics 322 indicate the number of encounters by type (e.g., emergency, inpatient or outpatient) that are reflected in the clinical research database, and provide a graphical depiction thereof. The metrics 324 indicate the most numerous types of procedures for various encounter types, and provide the number of procedures performed. The metrics 326 indicate the most numerous diagnoses for various encounter types, and provide the numbers of encounters and patients for each such diagnosis.

A control 330 enables the user to select the institution(s) for which the metrics 322, 324 and/or 326 are displayed (i.e., which institutions' data is reflected in the metrics), and a control 332 enables the user to select the range of years (or, alternatively, the range of months or days) for which the metrics 322, 324 and/or 326 are displayed. In various different embodiments, the application server (e.g., application node 36 of FIG. 1) may have pre-calculated the metrics for all possible combinations of settings for controls 330 and 332, or the metrics may be calculated anew each time control 330 or control 332 is adjusted (or each time one or both of controls 330 and 332 is/are adjusted and the user activates a "submit" button not shown in FIG. 5A, etc.).

As will be evident from the discussions below, some of the metrics provided on display 320 may correspond to individual disease codes (e.g., ICD9 codes), while others may correspond to "disease groups" that are pre-determined groupings of the individual codes. A "disease group" may be a set of ICD9 codes (or, in some embodiments and/or scenarios, ICD10 or other codes) that one or more qualified individuals have pre-defined so that end users need not spend as much time and effort when using the clinical research database. The group definitions may correspond to national (e.g., Centers for Medicare & Medicaid Services, or CMS) or local standards, for example, and/or may correspond to definitions that were utilized in the past for previous clinical research studies. Prior to being made available for use with the clinical research database, each group definition may be reviewed by a committee (e.g., clinicians, public health researchers, etc.). The group definitions may be considered as "internal use only" for a particular institution, and end users may be encouraged to review the appropriateness of a particular definition for their purposes.

In the example display 320, the metrics 324 and the metrics 326 both allow the user to expand or hide various metric subsets (e.g., "Top IP Procedures," "Top OP Procedures," etc., in metrics 324, and "Top DRGs," "Top IP Diagnoses (Grouped)," etc., in metrics 326). The example display 320 shows a scenario where, either by default or by user selection, the metrics 324 show the metric subset "Top IP Procedures" (e.g., the most numerous procedures for inpatient encounters), and the metrics 326 show the metric subset "Top DRGs" (e.g., the diagnosis-related groups corresponding to the most encounters, the most unique patients, or some other measure of frequency of occurrence).

If the user expands a different metric subset of metrics 324 or metrics 326, the display 320 may change to reveal that subset. For example, user activation of the "+" icon next to "Top IP Diagnoses (Grouped)" may cause the display 320 to change to the display 340 of FIG. 5B, where the most common disease groups are shown for inpatient encounters. As seen in FIG. 5B, 7,866 inpatient encounters resulted in a diagnosis of at least one of the ICD9 codes included in the disease group "ACUTE MYOCARDIAL INFARCTION (AMI)," and 4,472 unique patients with inpatient encounters were diagnosed with at least one of the ICD9 codes included in that disease group.

Figure 5E:
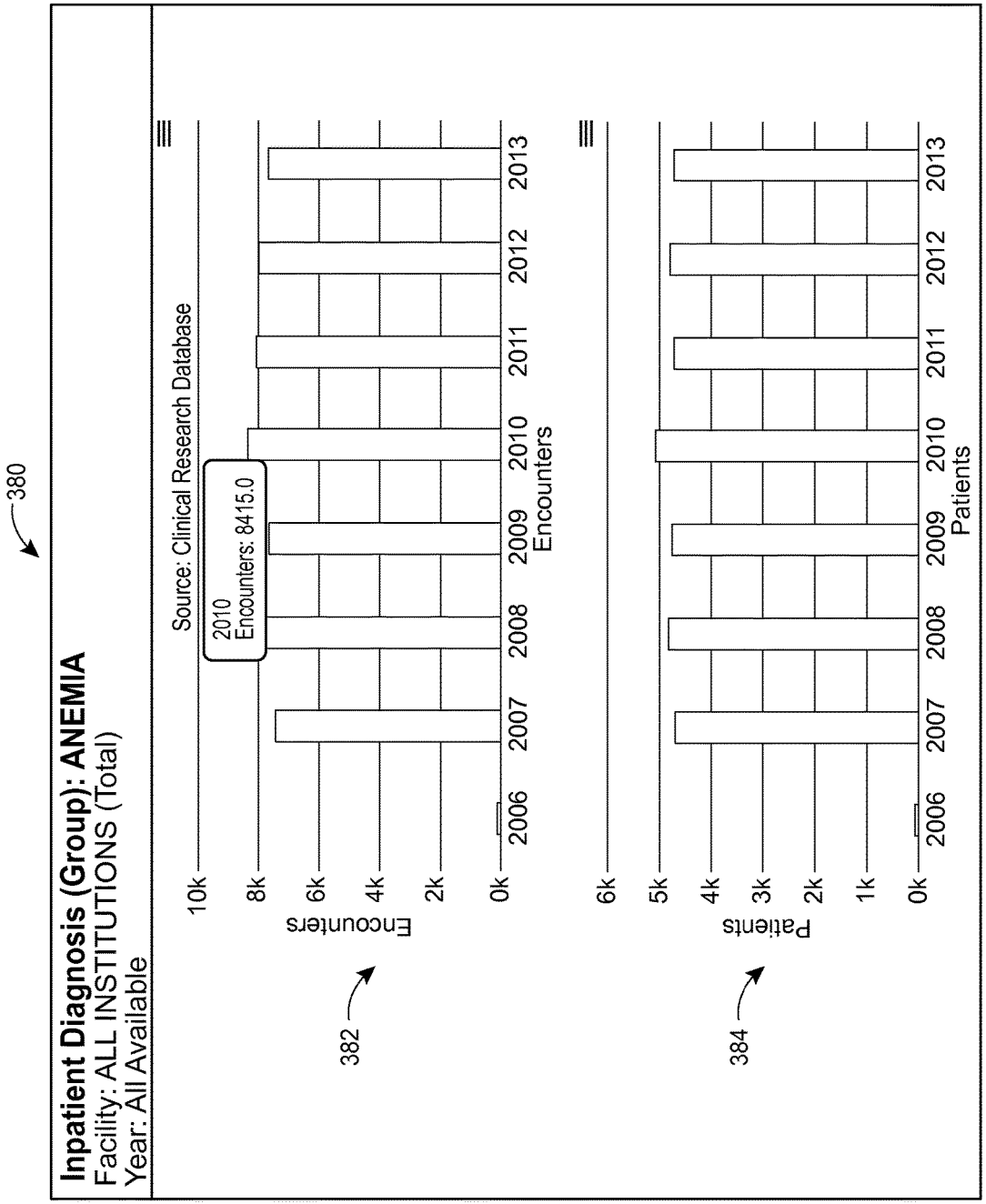

In an embodiment, the user can select a disease group name (or another control or link in the display 340) to view the definition of the disease group. If the user clicks on or otherwise selects "ANEMIA," for example, the web-based application may cause the display 350 of FIG. 5C to be presented to the user. As seen in FIG. 5C, the display 350 may include a scrollable list of the individual ICD9 codes within the group definition. The display 340 of FIG. 5B may also include, for metrics 324 and/or metrics 326, a control that, if activated by the user, provides the user with more detailed information about the associated metric subsets, and/or provides links to more detailed information about those metric subsets. If the user activates such a control for "Top IP Diagnosis (Grouped)" in display 340, for example, the web-based application may cause the display 360 of FIG. 5D to be presented to the user. In the display 360, a table 362 includes, for each top disease group diagnosis, a name 364 of the disease group, a link 366 to see the ICD9 code(s) included in the definition of the disease group, specific metrics 370 (e.g., number of encounters and number of unique patients) corresponding to the disease group, and a control 372. When selected by the user, the control 372 for a particular disease group may cause a graphical representation of metrics to be displayed to the user. If the user selects the control 372 next to the disease group "ANEMIA," for example, the web-based application may present the display 380 of FIG. 5E to the user, including a chart 382 showing number of encounters by year and another chart showing number of unique patients by year.

Referring again to FIG. 5B, some of the metric subsets included in metrics 326 may correspond to individual ICD9 codes rather than multi-code disease groups. If the user selects the "+" icon next to "Top IP Primary Diagnosis Codes," for example, the web-based application may cause the display 400 of FIG. 5F to be presented to the user. In the display 400, each row of metrics 324 corresponds to an individual ICD9 code rather than a disease group, and shows the number of inpatient encounters and the number of unique patients for that ICD9 code (e.g., ICD9 code 401.9 was diagnosed in 54,118 inpatient encounters, and for 34,101 different patients). As with the top inpatient diagnoses according to disease group (shown in FIG. 5B), the metrics 326 may allow the user to select a control to drill down into further detail. For example, FIG. 5G shows a user interface display 420 that the web-based application may present to the user if the user selects such a control. In the display 420, a table 422 includes, for each top ICD9 code diagnosis, a description 424 for the ICD9 code, the code 426 itself, specific metrics 430 (e.g., number of encounters and number of unique patients) corresponding to the ICD9 code, and a control 432. When selected by the user, the control 432 for a particular ICD9 code may cause a graphical representation of metrics to be displayed to the user (e.g., similar to that shown in FIG. 5E for disease group diagnoses).

Figure 6:
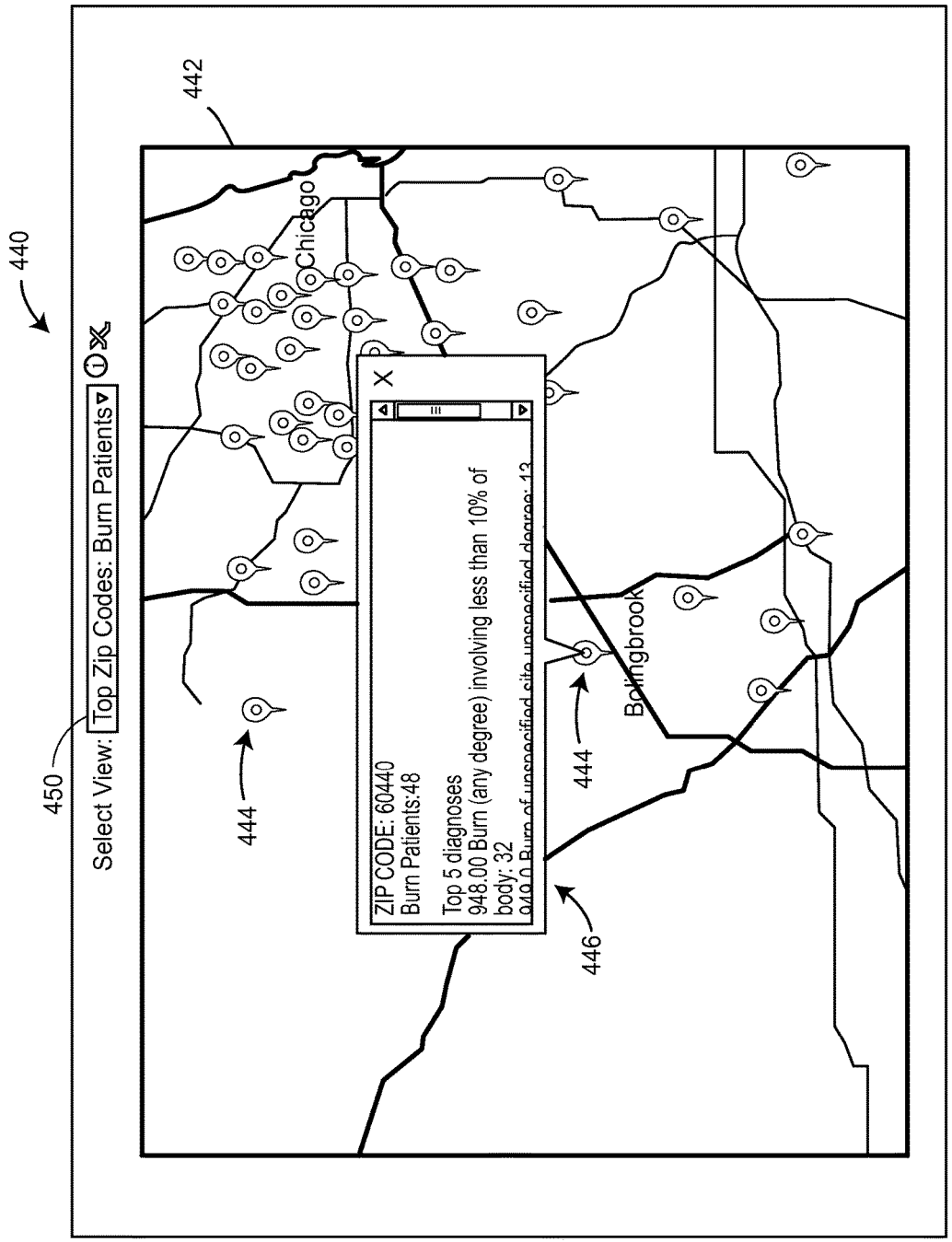
FIG. 6 depicts an example user interface display corresponding to a maps tab of the clinical research database web-based application, according to an embodiment.

Referring now back to display 320 of FIG. 4, if the user selects the maps tab 302C, the web-based application may cause the client device to present the user interactive display 440 to the user, as seen in FIG. 6. The display 440 may include a map 442, which may depict a geographic area around one or more of the institutions sourcing the data in the clinical research database (and/or facilities associated with those institutions), for example. Situated on the map 442 may be a number of pins 444 showing locations at which patient encounters occurred with a particular type of diagnosis (e.g., burn patients). If the user selects (e.g., hovers over, or clicks on, etc.) a particular one of pins 444, a window 446 may appear providing more detailed information on the number of patients treated at the location and/or the specific diagnoses for those patients (e.g., by ICD9 code). The user may select which types of patients/diagnoses are to be shown on the map 442 by utilizing a control 450. In the scenario corresponding to FIG. 6, for example, the user has selected "burn patients," and so the pins 444 indicate locations of patient encounters that results in a burn-related diagnosis.

Figure 7B:
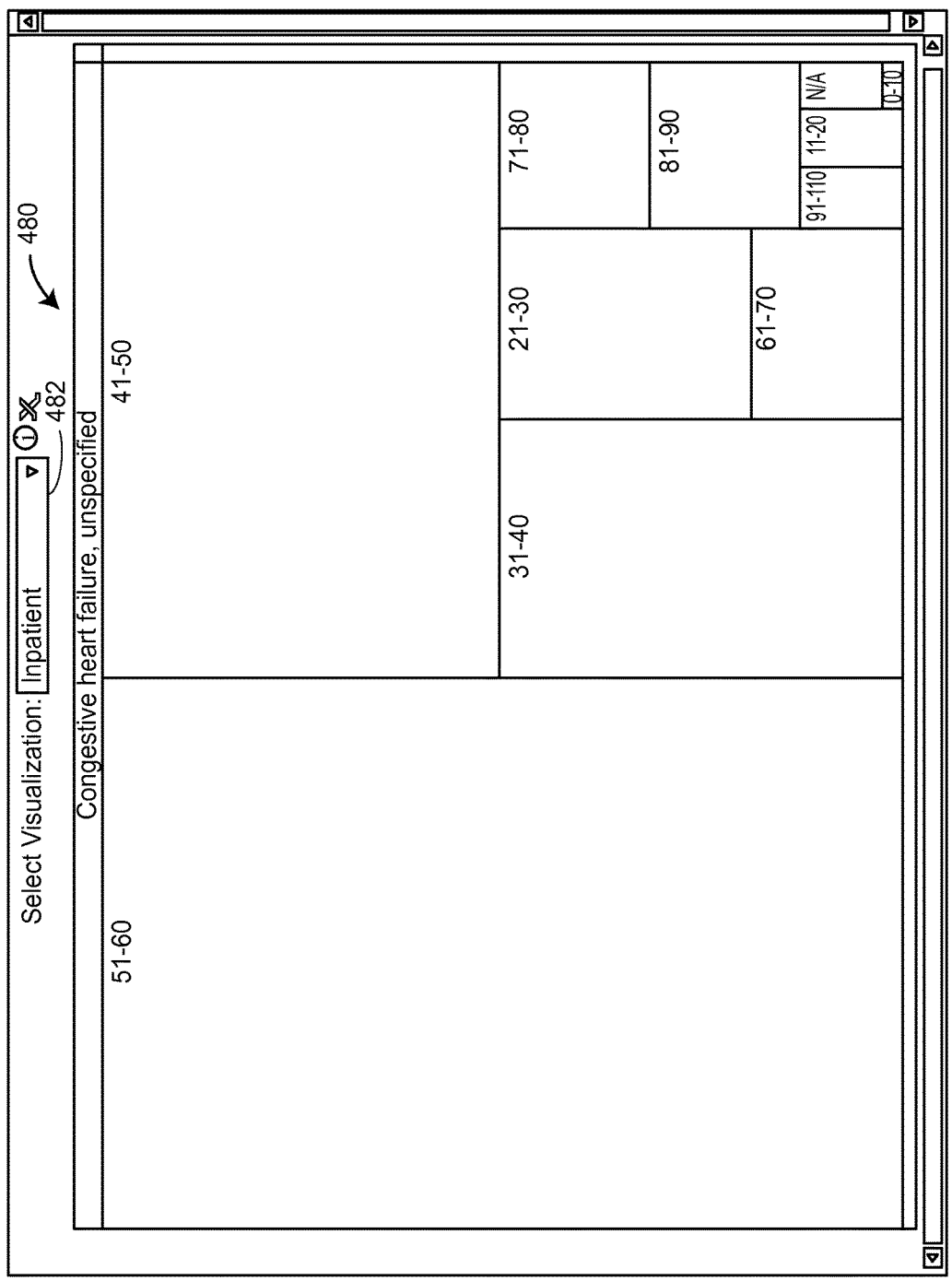

Referring again to display 320 of FIG. 4, if the user selects the visualizations tab 302D, the web-based application may cause the client device to present the user interactive display 460 to the user, as seen in FIG. 7A. Generally, the visualizations tab 302D allows users to access pre-defined data visualizations of pre-determined patient cohorts or pre-analyzed data metrics. For example, the display 460 may include a "tile" diagram that includes a series of tiles of varying size, where the size of each tile represents the frequency at which a reported inpatient diagnosis code (e.g., ICD9 code) occurs (e.g., with a larger tile representing a higher frequency of occurrence). The tiles may generally be arranged left to right (or in any other suitable manner) with larger, more highly reported measures starting on the left. In other embodiments, other visualizations may be shown on the display 460, such as histograms, bar charts, etc. A user may be able to drill down into each element (e.g., tile, histogram, bar, etc.) to view the information summarized/reported by the element in a more detailed format. If a user clicks on the tile labeled "Congestive heart failure, unspecified" in the display 460, for example, the web-based application may cause the client device to present the user interactive display 480 to the user, as seen in FIG. 7B. In the display 480, each tile represents the age range indicated on the tile, and again tiles may generally be arranged left to right, with larger, more highly reported measures starting on the left. Moreover, the user may be able to click on any of the tiles in the display 480 to obtain even more detailed information. Each visualization (e.g., the visualization of the display 460, the display 480, or another visualization not shown) may include an option/control that enables the user to download the information detailed in the visualization. Moreover, additional visualizations may be added by request, and made available to all users.

Figure 8A:
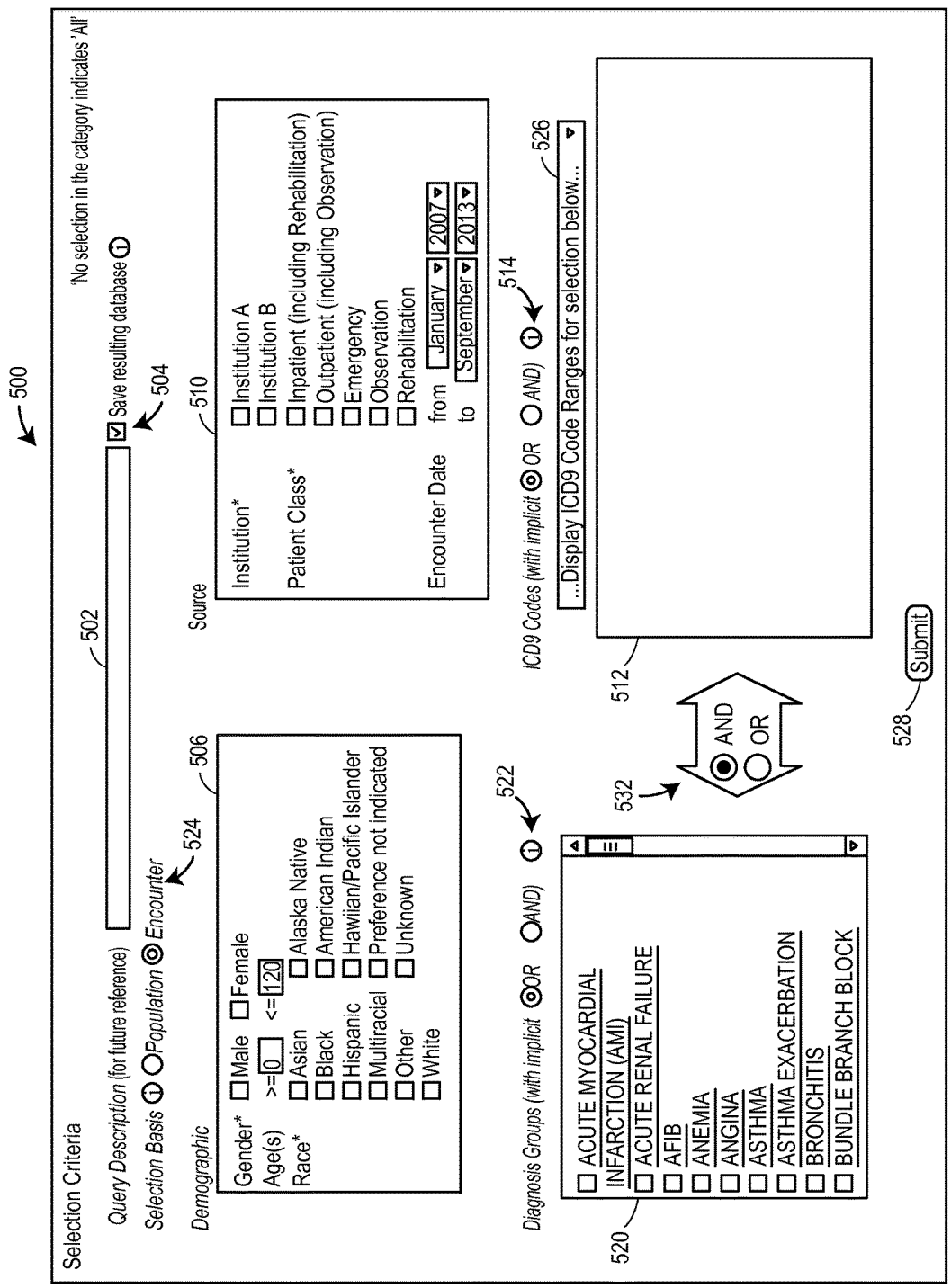

Referring again to display 320 of FIG. 4, if the user selects the query tool tab 302E, the web-based application may cause the client device to present the user interactive display 500 to the user, as seen in FIG. 8A. Generally, the display 500 may provide an easy-to-use, intuitive interface, with a set of query options that is limited enough to avoid user confusion, yet large enough to provide users flexibility in building an initial ("base") query. In the example embodiment of FIG. 8A, the display 500 includes a query description field 502 in which the user may enter a brief description that may be saved and associated with the query, and a save control 504 that the user may select if he or she desires that the query results be saved. Further, the display 500 includes a number of controls for entering search criteria, including demographic controls 506, source controls 510, an ICD 9 code control 512, an ICD9 code logic control 514, a disease group control 520, a disease group logic control 522 and a selection basis control 524. In other embodiments, the display may include more, fewer and/or different controls than those shown in FIG. 8A.

The demographic controls 506 may enable the user to enter one or more search criteria relating to patient demographics. In the example embodiment of FIG. 8A, the demographic controls 506 includes three controls allowing the user to enter criteria for patient gender, patient age range and/or patient race/ethnicity, respectively. The source controls 510 enable the user to enter one or more search criteria relating to the source of the data being searched. In the example embodiment of FIG. 8A, the source controls 510 includes three controls allowing the user to enter criteria for the institution(s) providing the encounter data, the type of encounter (e.g., inpatient, outpatient, emergency, etc.), and the date range in which the encounter took place, respectively. While FIG. 8A depicts only two institution options, other embodiments or scenarios may have more options, or no option (e.g., just one institution).

The ICD9 code control 512 may enable the user to enter one or more ICD9 codes as search criteria. To assist in selecting the ICD9 code(s), the user may access a drop-down menu 526 providing a list of ICD9 codes and descriptions thereof. Alternatively, the drop-down menu 526 may provide the list of ICD9 codes in another manner. For example, the drop-down menu 526 may instead be a button or other control that, if selected/activated by the user, causes a pop-up window with the list of ICD9 codes to appear. If two or more ICD9 codes are selected using control 512 (e.g., typed into the field of control 512), the user may select a Boolean operator using ICD9 code logic control 514 (e.g., an "AND" or "OR" operation). The selected Boolean operator may be applied to all of the selected ICD9 codes for purposes of the search criteria, for example.

The disease group control 520 may enable the user to enter one or more disease groups as search criteria, where each disease group corresponds to a respective set of one or more ICD9 codes (e.g., as discussed above in connection with data metrics tab and display 340 of FIG. 5B). The user may select each desired disease group by clicking on a box next to that disease group, for example, or in another suitable manner. To assist in selecting the disease group(s), the user may be provided with quick access to descriptions of the various disease groups (e.g., lists of the constituent ICD9 codes). For example, the user may click on or otherwise select the text of the disease group name to view the description, which may cause a display such as pop-up window 530 of FIG. 8B to appear. If two or more disease groups are selected using control 520, the user may select a Boolean operator using disease group logic control 522 (e.g., an "AND" or "OR" operation). The selected Boolean operator may be applied to all of the selected disease groups for purposes of the search criteria, for example.

In some embodiments, an additional control 532 enables the user to select a Boolean operator (e.g., "AND" or "OR") that operates between the ICD9 criteria defined by controls 512 and 514 and the disease group criteria defined by controls 520 and 522. The control 532 may only appear if the user has selected at least one disease group using control 520 (or only if the user has selected at least one ICD9 code using control 512 and at least one disease group using control 520, etc.), or may always appear on the display 500. Alternatively, the control 532 may be omitted, and the search expression may automatically use a particular Boolean operator (e.g., an "OR" operator) between any ICD9 criteria defined by controls 512 and 514 and any disease group criteria defined by controls 520 and 522.

The selection basis control 524 may enable the user to identify a patient cohort using "population-based" searching or "encounter-based" searching. Generally, a search is "population-based" if the search criteria are assessed on a patient-by-patient basis, and is "encounter-based" if the search criteria are assessed on an encounter-by-encounter basis. The goal of population-based queries is generally to evaluate all criteria over all encounters for a given patient, such that the criterion or criteria do not have to occur in the context of a single encounter for the patient, but rather can occur over the course of multiple encounters for the patient. If the criteria are "all diabetic patients that have had anemia in the past year," for example, a population-based query would return all patients that have had both (1) a diagnosis of diabetes at any time during the past year, and (2) a diagnosis of anemia at any time during the past year. Conversely, an encounter-based query would return only those patients that had both a diagnosis of diabetes and a diagnosis of anemia in the same encounter record (for an encounter occurring during the past year). In some embodiments, encounter-based searching is the default setting for control 524, while in other embodiments population-based searching is the default setting.

To submit a query for processing, the user may select a submit control (e.g., button) 528. When the user submits the query, a corresponding real-time query may be initiated on the Hadoop cluster. A process running on an application node (e.g., application node 36 of FIG. 1) may process/digest the query request, and submit the query to the Hadoop cluster (e.g., Hadoop cluster 20 of FIG. 1) for processing. The Hive processing may generate a standard set of Hadoop MapReduce operations based on the query parameters/criteria.

The processing steps may depend on whether the user selected population-based or encounter-based searching. If encounter-based, all of the user-selected demographic and source criteria entered with the query tool via user interface display 500 (using controls 506 and 510), if any, may be applied globally to the encounters represented in the clinical research database. The encounters meeting the criteria may be identified/returned, after which the ICD9 selection logic reflected by the settings of controls 512, 514, 520, 522 and 532 may be applied to those identified encounters (e.g., all of the individual ICD9 codes specified by the control 512 may be searched with "AND" or "OR" logic as specified by control 514, all of the disease groups specified by the control 520 may be searched with "AND" or "OR" logic as specified by control 522, and the individual ICD9 code search criteria and the disease group search criteria may be joined with "AND" or "OR" logic as specified by control 532). If disease group criteria are specified using control 520, all ICD9 codes within a particular disease group may automatically be searched using a Boolean "OR," such that meeting at least one of the constituent ICD9 codes causes that disease group criterion to be satisfied.

The unique patients (e.g., unique patient identifiers) associated with all of the encounters satisfying the individual ICD9 code criteria (if any) and disease group criteria (if any) may represent the patient cohort for the encounter-based query. The results may then be saved on the Hadoop cluster (e.g., under a filename that is a concatenation of user identifier and job number), and/or automatically processed by one or more discrete analyses, as discussed further below.

If the user instead selected population-based searching, the initial step may be the same as for encounter-based searching. That is, all of the user-selected demographic and source criteria entered with the query tool via user interface display 500 (using controls 506 and 510), if any, may be applied globally to the encounters represented in the clinical research database. Unlike the encounter-based search described above, however, an ICD9 "distribution map" may be generated for all unique/distinct patient identifiers associated with any one or more of the encounters that met the user-selected demographic and source criteria. That is, for each unique patient identifier in that set of encounters, a list of all ICD9 codes diagnosed for that patient (during any one or more encounters in the encounter set) may be identified. Once a distribution map is generated for each unique patient identifier, the ICD9 selection logic reflected by the settings of controls 512, 514, 520, 522 and 532 may be applied to each ICD9 code list on a patient-by-patient basis. The patients with an ICD9 code list satisfying the ICD9 selection logic may then represent the patient cohort for the population-based query, and all of the encounters that are associated with a patient in the patient cohort and met the user's initial criteria (e.g., date range, gender, age, etc.) may be aggregated to form the result set that corresponds to the patient cohort. As with the encounter-based search, the results may then be saved in the Hadoop cluster (e.g., under a filename that is a concatenation of user identifier and job number), and/or automatically processed by one or more discrete analyses, as discussed further below.

While population-based searching has been described thus far with respect to an embodiment in which ICD9 criteria are applied to the distribution map, other criteria may be applied to the distribution map in other embodiments. For example, CPT code criteria, lab value criteria and/or any other suitable criteria may be applied to the distribution map instead of (or in addition to) the ICD9 criteria.

For both encounter-based and population-based searching, the results of the base query may be stored on the Hadoop cluster as a table, which is referred to herein as a "Z-table." Each Z-table may be a collection of particular de-identified attributes, such as subject/patient identifiers, encounter identifiers and hospital account records (HARs) for the encounter/patients in the corresponding result set. The information in a Z-table may allow other data related to the result set, such as a set of clinical laboratory results for one of the patients or encounters in the result set, to be retrieved for any purpose at a later time. For example, the Z-tables may be used for downstream processing to perform further analysis on the result set, and/or to further reduce the result set with additional criteria, as discussed below. While the HARs may, in some embodiments, be omitted from the Z-table, HARs may be useful in instances where data records associate clinical laboratory values with a HAR but not with an encounter. Each Z-table may be stored on the cluster for a limited, predetermined time (e.g., 90 days) before being automatically deleted, or may be stored indefinitely.

Referring again to display 320 of FIG. 4, if the user selects the saved query tab 302F, the web-based application may cause the client device to present the user interactive display 540 to the user, as seen in FIG. 9A. The display 540 may depict a number of past query results, which may be specific to the user and/or may include the query results for one or more other users. A description field 542 may show the name of each saved query (e.g., the filename that was entered in field 502 of FIG. 8A, or a name automatically generated based on the corresponding search criteria, etc.), and an action field 544 may allow the user to perform any of one or more actions, such as "reduce," "analyze," "output" and/or "extract" actions that are described further below.

If the user selects a query result (e.g., by clicking on an "O" in the action field 544), the user may be presented with a display of one or more metrics that were determined for the corresponding result set. If the user selects the "Afib, Age>50, Males, All Years" query result, for example, the web-based application may cause the user interface display 560 of FIG. 9B to be presented to the user. The display 560 includes query identification/description information 562, a control 564 that allows the user to drill down into more detailed information about the metrics shown, and a table 566 displaying the metrics themselves. The metrics may include metrics that were automatically generated after the query was submitted, and/or may include metrics corresponding to one or more other analyses specifically requested by the user. The analyses that generate the metrics may be performed by analysis programs/scripts 40 of FIG. 1, for example. FIG. 9C shows another user interface display 580 that may be presented to the user when the user clicks on the query result (or as an extension of the display 560, etc.). The display 580 depicts the criteria 582 that were used to arrive at the cohort/result set, and includes a table 584 with another set of metrics (e.g., race and gender breakdown of patients in the cohort, total number of encounter in the result set, etc.).

As noted above, analyses may be performed on the initial result set automatically, and/or may be performed at the user's request. For example, default/automatic analyses may include processing of the result set to determine age, gender and/or ethnicity/race distribution of the unique patients in the cohort, distribution of encounter types (inpatient, outpatient, etc.) of the encounters in the result set, number of unique patients in the result set, number of encounters in the result set, number of available clinical labs data sets in the result set, number of available procedures in the result set, and/or payor mix and/or financial class distribution for the result set.

The user may reduce a result set in the query results by activating the appropriate control. Referring again to FIG. 9A, for example, if the user selects "R" for the query result "Anemia, Females, Age<=50" (which may itself be a reduced result set, or a base/initial query result set), the web-based application may cause the user interface display 600 of FIG. 9D to be displayed to the user. The display 600 includes query identification/description information 602, a description field 604 in which the user can enter a name for the reduced result set, and various controls for selecting additional search criteria. In the embodiment of FIG. 9D, for example, the display 600 includes a first control 606 for selecting a general category/type of criteria (e.g., CPT codes), a second control 610 for selecting the criteria category/type with more specificity (e.g., anesthesia-related CPT codes), and a third control 612 for selecting the precise criteria (e.g., one or more specific CPT codes relating to anesthesia). In other embodiments and/or scenarios, controls 606, 610 and 612 may be replaced by only two controls or only a single control, or additional controls may be included as needed to facilitate the user's selections of additional search criteria. The display 600 may also include a "submit" control (e.g., button) 614 which, when activated by the user, causes a corresponding real-time query to be initiated on the Hadoop cluster (e.g., as described above with respect to the initial query). To obtain the data needed to reduce a result set, the Hadoop cluster may execute programs and/or scripts (e.g., query programs/scripts 42 of FIG. 1) that access the Z-table(s) associated with the saved query results.

Alternatively, the user may perform additional analyses on a result set in the query results by activating the appropriate control. Referring again to FIG. 9A, for example, if the user selects the "A" for the query result "CPT=93010" (which may itself be a reduced result set, or a base/initial query result set) the web-based application may cause the user interface display 620 of FIG. 9E to be displayed to the user. The display 620 includes query identification/description information 622, and a control 624 for selecting one or more analysis modules. For example, the control 624 may list, and allow selection of, a number of different available analysis types, such as analyzing by account type, by length of stay for each inpatient, and so on. The display 620 may also include a "submit" control (e.g., button) 626 which, when activated by the user, causes the selected analysis or analyses to be performed. To obtain the data needed to analyze a result set, the Hadoop cluster may execute programs and/or scripts (e.g., analysis programs/scripts 40 of FIG. 1) that access the Z-table(s) associated with the initial query results.

The user may also choose to extract the dataset corresponding to a particular query result (e.g., by clicking on an "E" in the action field 544). In other embodiments, the action field 544 includes one or more additional options, and/or one or more of the "R" (reduce), "A" (analyze), "O" (output) and "E" (extract) options are not included in the action field 544.

Referring again to display 300 of FIG. 4, the remaining tabs may similarly present user interactive displays, or purely informational displays, to the user. For example, the data request tab 302G may cause the web-based application to present a data request form to the user. The user may fill out and submit the data request form request certain date, and/or to request a consult with a clinical data analyst, etc. As another example, the data model tab 302H may cause a list of the Hadoop data model fields to be displayed to the user, possibly with fields descriptions (e.g., as listed above in Section IV). As yet another example, the training/documentation tab 302I may cause training/tutorial information, other information, and/or links or references to be displayed to the user. For example, tutorial videos, disease group definitions, and/or any other content may be displayed to the user.

While the user interface displays of FIGS. 4-9 have been described with respect to a web-based application, it is understood that, in other embodiments, the displays may be provided to the user in a different manner. As noted above in Section II, for example, the displays may be generated and presented by a software application that is downloaded from a server (e.g., the web server 22 of FIG. 1) and executes on a smartphone, tablet or other computing device of a user (e.g., client device 24 of FIG. 1).

Figure 10:
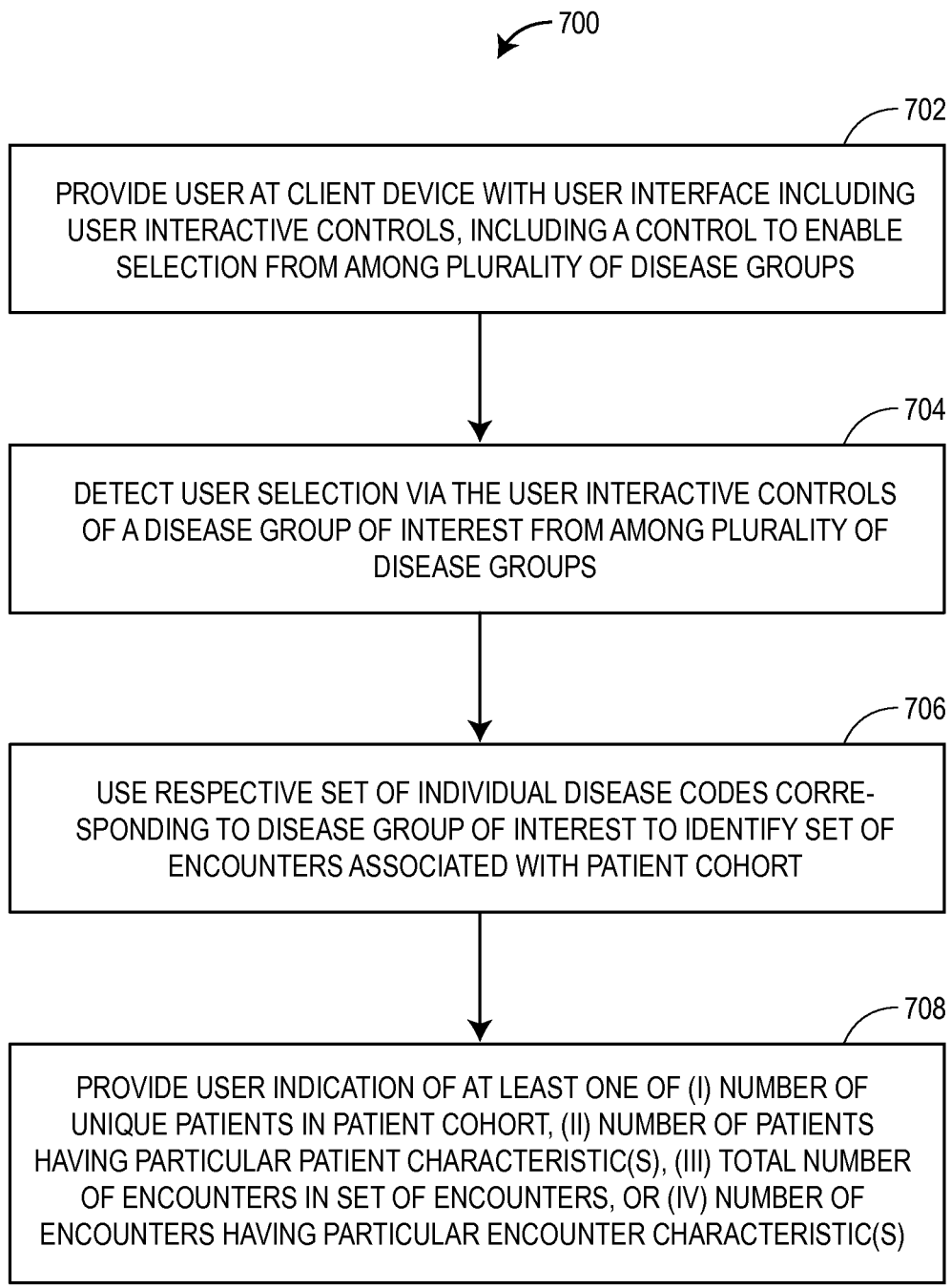
FIG. 10 depicts a flow diagram of an example method for facilitating patient cohort identification, according to an embodiment.

VI. Exemplary Process Flow for Facilitating Identification of a Patient Cohort Using Predetermined Disease Groupings FIG. 10 depicts a flow diagram of an example method 700 for facilitating patient cohort identification using predetermined disease groupings, according to an embodiment. In one embodiment, the method 700 is implemented in (e.g., performed by one or more processors of) one or more servers, such as the web server 22 and/or the Hadoop cluster 20 of FIG. 1, for example.

In the example method 700, a user at a client device may be provided with a user interface including user interactive controls (block 702). The user interface may be a GUI in a web browser window (e.g., a GUI having content and presentation defined by HTML, JSP and/or other scripting language instructions), and block 702 may be implemented by web server 22 of FIG. 1, for example. The user interactive controls may include a control to enable selection from among a plurality of disease groups, with each disease group corresponding to a respective set of two or more individual disease codes (e.g., two or more ICD9 codes, two or more ICD10 codes, etc.). In some embodiments and/or scenarios, however, the pool of disease groups from which a selection can be made additionally includes one or more disease "groups" that correspond to only a single disease code. The user interface may provide a list of the plurality of disease groups (e.g., with check boxes for selecting or de-selecting particular disease groups), for example. The user interactive controls may also include one or more other controls, such as one or more controls to enable selection of demographic characteristics of patients, one or more controls to enable selection of encounter types and/or encounter date ranges, one or more controls to enable selection of sources of patient encounter information, a control to enable selection of either a population-based searching algorithm or an encounter-based searching algorithm and/or a control to enable selection of individual disease codes (e.g., ICD9 codes), for example.

A user selection via the user interactive controls of a disease group of interest, from among the plurality of disease groups, may be detected (block 704). Block 704 may be implemented by a web server such as web server 22 of FIG. 1, for example. The user selection may have been made via any suitable input mechanism(s), such as a touch screen, a mouse, a keyboard, a touch pad, etc., and communicated to the web server via a network (e.g., the Internet).

The respective set of individual disease codes corresponding to the disease group of interest may be used to identify a set of encounters associated with a patient cohort (block 706). Block 706 may be implemented by the Hadoop cluster 20 of FIG. 1, or by web server 22 of FIG. 1 (e.g., by sending a query request, and data indicative of the set of individual disease codes, to the Hadoop cluster 20 for processing, and receiving in return data indicative of the set of encounters), for example. To identify the set of encounters, the respective set of individual disease codes may be applied as search criteria in a search of patient encounter information arranged in a non-relational database (e.g., patient encounter information stored in data nodes 30-1 through 30-M of FIG. 1). If the user also selected other search criteria (e.g., demographic characteristics, encounter type and/or encounter date range, source(s) of encounter information, individual disease codes and associated logic, etc.), those search criteria may be used, along with the set of individual disease codes corresponding to the disease group of interest, to identify the set of encounters associated with the cohort. Moreover, if the user also selected one or more other disease groups, and designated some selection logic (e.g., a Boolean "AND" or "OR" operator between all selected disease groups, or, in some embodiments, a more complex logic operation), the search may be performed using the designated selection logic. If the user specified encounter-based or population-based searching using the controls, the set of encounters may be identified using the specified searching algorithm.

The user may be provided with an indication of one or more metrics relating to the identified patient cohort and/or the encounters for the patient cohort, such as the number of unique patients in the patient cohort, the number of patients in the patient cohort having a particular set of one or more patient characteristics, the total number of encounters in the set of encounters associated with the patient cohort, the number of encounters, in the set of encounters associated with the patient cohort, having one or more particular encounter characteristics, and/or one or more other metrics (block 708). Block 708 may be implemented by web server 22 of FIG. 1, for example. The indication may be descriptive text (e.g., "Number of Unique Patients="") and an associated number or numbers (e.g., "4,026"), or any other type or format of information suitable to convey the metric to the user. The indication may be provided to the client device for display in a web browser window, for example. Alternatively, the indication may be sent to the user in a different manner (e.g., in a report attached to an email, etc.).

The method 700 may also include one or more additional blocks not shown in FIG. 10. For example, the method 700 may include one or more additional blocks in which user selections (e.g., selections made via the user interactive controls) of one or more other search parameters of interest is/are detected (e.g., parameters corresponding to demographic characteristic controls, encounter type and/or encounter date range controls, a control for selecting sources of encounter information, a control for selecting individual disease codes, a control for selecting population-based versus encounter-based searching, etc.). As another example, the method 700 may include a block in which, in response to detecting a user request (made via the user interface) for a description of a first disease group of the plurality of disease groups, the user interface is caused to display a list of the respective set of ICD9 codes corresponding to the first disease group.

Figure 11:
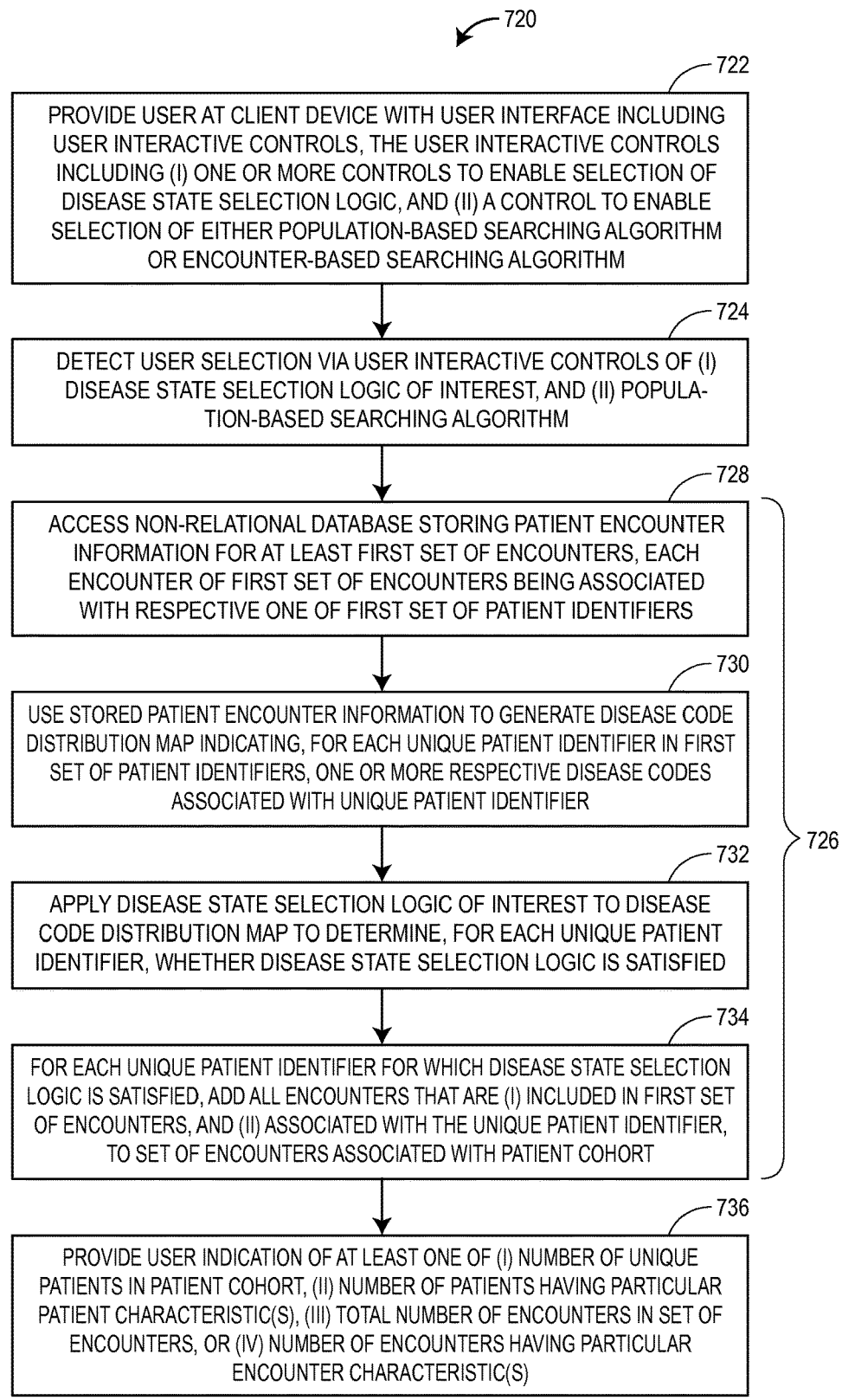
FIG. 11 depicts a flow diagram of another example method for facilitating patient cohort identification, according to an embodiment.

VII. Exemplary Process Flow for Facilitating Identification of a Patient Cohort Using Population-Based Searching FIG. 11 depicts a flow diagram of an example method 720 for facilitating patient cohort identification using population-based searching, according to an embodiment. It is noted that the method 720 corresponds not only to a specific embodiment, but also to a specific scenario in which the user selects population-based searching rather than encounter-based searching. In one embodiment, the method 720 is implemented in (e.g., performed by one or more processors of) one or more servers, such as the web server 22 and/or the Hadoop cluster 20 of FIG. 1, for example.

In the example method 720, a user at a client device may be provided with a user interface including user interactive controls (block 722). The user interface may be a GUI in a web browser window (e.g., a GUI having content and presentation defined by HTML, JSP and/or other scripting language instructions), and block 722 may be implemented by web server 22 of FIG. 1, for example. The user interactive controls may include one or more controls to enable selection of disease state selection logic. A user may select a particular type of disease state selection logic by selecting two or more disease states (e.g., two or more ICD9 codes, and/or two or more disease groups each corresponding to a number of ICD9 codes, etc.), as well as at least one Boolean operator to define the logic used for the search criteria (e.g., "AND" of all selected disease states, "OR" of all selected disease states, or, in some embodiments, a more complex logical expression, such as an "AND" or "OR" of all selected ICD9 codes, an "AND" or "OR" of all selected disease groups, and/or an "AND" or "OR" of the collective ICD9 code criteria and the collective disease group criteria). The user interactive controls may also include a control to enable selection of either a population-based searching algorithm (for applying search criteria across multiple encounters on a patient-by-patient basis) or an encounter-based searching algorithm (for applying search criteria on an encounter-by-encounter basis). The user interactive controls may also include other controls, such as one or more controls to enable selection of demographic characteristics of patients, one or more controls to enable selection of encounter types and/or encounter date ranges, one or more controls to enable selection of patient encounter information, a control to enable selection of individual disease codes (e.g., ICD9 codes) and/or disease groups, etc.

A user selection via the user interactive controls of disease state selection logic of interest (e.g., two or more ICD9 codes and a Boolean operator, or two or more disease groups and a Boolean operator, etc.), and of the population-based searching algorithm, may be detected (block 724). Block 724 may be implemented by a web server such as web server 22 of FIG. 1, for example. The user selection may have been made via any suitable input mechanism(s), such as a touch screen, a mouse, a keyboard, a touch pad, etc., and communicated to the web server via a network (e.g., the Internet). The disease state selection logic of interest may also include at least one Boolean operator to operate on two or more disease states.

A set of encounters associated with a patient cohort may be identified (blocks 726). Blocks 726 may be implemented by the Hadoop cluster 20 of FIG. 1, for example. Identifying the set of encounters may include a number of steps or processes. For example, a non-relational database storing patient encounter information for at least a first set of encounters may be accessed (block 728). Each encounter of the first set of encounters may be associated with a respective one of a first set of patient identifiers. The stored patient encounter information may be used to generate a disease code distribution map (block 730). The map may indicate, for each unique patient identifier in the first set of patient identifiers, the disease code(s) (e.g., ICD9 code(s)) associated with that particular unique patient identifier. The disease state selection logic of interest may be applied to the disease code distribution map to determine, for each unique patient identifier, whether the disease state selection logic is satisfied (block 732). For each unique patient identifier for which the disease state selection logic is satisfied, any encounters within the first set of encounters that are associated with that particular unique patient identifier may be added to the set of encounters associated with the patient cohort (block 734).

In some embodiments, the "first set of encounters" referred to above in connection with block 728 is itself a subset of a larger collection of encounters, and one or more other search criteria is/are used at an earlier stage (e.g., prior to performing some or all of blocks 728, 730, 732 and 734) to identify the first set of encounters from among that collection of encounters. For example, a user-selected demographic characteristic of interest (e.g., age, gender, race/ethnicity), encounter characteristic of interest (e.g., encounter type), encounter date range of interest, and/or source of interest (e.g., institution providing the encounter data) may be applied as initial search criteria to identify the first set of encounters from among the larger collection of encounters. Once the first set of encounters has been identified, the disease code distribution map may be generated (at block 730) using a smaller set of unique patient identifiers (e.g., only those unique patient identifiers that correspond to the first set of encounters, rather than all unique patient identifiers within the larger collection of encounters).

The user may be provided with an indication of one or more metrics relating to the identified patient cohort and/or the encounters for the patient cohort, such as the number of unique patients in the patient cohort, the number of patients in the patient cohort having a particular set of one or more patient characteristics, the total number of encounters in the set of encounters associated with the patient cohort, the number of encounters, in the set of encounters associated with the patient cohort, having one or more particular encounter characteristics, and/or one or more other metrics (block 736). Block 736 may be implemented by web server 22 of FIG. 1, for example, and may be similar to block 708 of the method 700 in FIG. 10.

The method 720 may also include one or more additional blocks not shown in FIG. 11. For example, the method 720 may include one or more additional blocks in which user selections (e.g., selections made via the user interactive controls) of one or more other search parameters of interest is/are detected (e.g., parameters corresponding to demographic characteristic controls, encounter type and/or encounter date range controls, a control for selecting sources of encounter information, a control for selecting individual disease codes, a control for selecting disease groups, etc.).

VIII. Additional Considerations

The following additional considerations apply to the foregoing discussion. Throughout this specification, plural instances may implement operations or structures described as a single instance. Although individual operations of one or more methods are illustrated and described as separate operations, one or more of the individual operations may be performed concurrently, and nothing requires that the operations be performed in the order illustrated. These and other variations, modifications, additions, and improvements fall within the scope of the subject matter herein.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of "a" or "an" is employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for creation, operation and/or use of a clinical research database through the principles disclosed herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed:

1. A computer-implemented method for efficiently executing a population-based query of patient encounter information stored in one or more database formats, the method comprising:
   generating, by one or more processors, a data repository of a Hadoop cluster, at least in part by
      extracting patient encounter information from one or more data sources that collectively store the patient encounter information in the one or more database formats, wherein the patient encounter information includes (i) information descriptive of a plurality of encounters, (ii) a plurality of patient identifiers each associated with one or more of the plurality of encounters, and (iii) a plurality of disease codes each associated with one or more of the plurality of encounters and one or more of the plurality of patient identifiers,
      generating a plurality of instances of a Hadoop data model by transforming the extracted patient encounter information from the one or more database formats to a format of the Hadoop data model, wherein each instance of the Hadoop data model specifies (i) information descriptive of a single encounter of the plurality of encounters, (ii) a single patient identifier of the plurality of patient identifiers, and (iii) one or more disease codes corresponding to the single encounter and the single patient identifier, and
      storing the instances of the Hadoop data model in the data repository of the Hadoop cluster;
   providing, by one or more processors, a user at a client device with a user interface including user interactive controls, the user interactive controls including (i) one or more selection logic controls to enable selection of disease state selection logic, and (ii) an algorithm control to enable selection of either a population-based searching algorithm for applying search criteria across multiple encounters on a patient-by-patient basis, or an encounter-based searching algorithm for applying search criteria on an encounter-by-encounter basis;
   detecting, by one or more processors, submission of a user query that the user entered via the user interface, wherein the user query is associated with (i) a logical expression, specified by a user setting of the one or more selection logic controls, that includes a Boolean operator operating on two or more disease states, and (ii) the population-based searching algorithm, as specified by a user setting of the algorithm control;
   in response to detecting the submission of the user query, initiating a real-time query on the Hadoop cluster to identify a set of encounters that is associated with a patient cohort satisfying the logical expression on a patient-by-patient basis, irrespective of whether the patient cohort also satisfies the logical expression on an encounter-by-encounter basis, at least in part by
      accessing the data repository of the Hadoop cluster,
      generating a disease code distribution map from the instances of the Hadoop data model, wherein the disease code distribution map includes (i) each unique patient identifier among at least a subset of the plurality of patient identifiers, and (ii) for each of the unique patient identifiers, a corresponding disease code list comprising all disease codes specified by any instance of the Hadoop data model that also specifies the unique patient identifier,
      for each of the unique patient identifiers, determining whether the corresponding disease code list satisfies the logical expression, and
      for each of the unique patient identifiers having a corresponding disease code list that satisfies the logical expression, adding to the set of encounters all encounters associated with the unique patient identifier; and
   providing, by one or more processors, the user an indication of at least one of (i) a number of unique patients in the patient cohort, (ii) a number of patients in the patient cohort having a particular set of one or more patient characteristics, (iii) a total number of encounters in the set of encounters associated with the patient cohort, or (iv) a number of encounters, in the set of encounters associated with the patient cohort, having one or more particular encounter characteristics.

2. The computer-implemented method of claim 1, wherein the plurality of disease codes comprises a plurality of International Classification of Diseases, Ninth Revision (ICD9) codes.

3. The computer-implemented method of claim 2, wherein the logical expression includes the Boolean operator operating on two or more ICD9 codes.

4. The computer-implemented method of claim 2, wherein the logical expression includes the Boolean operator operating two or more disease groups, each of the disease groups corresponding to a respective set of two or more ICD9 codes.

5. The computer-implemented method of claim 2, wherein the logical expression includes the Boolean operator operating on first criteria for one or more ICD9 codes and second criteria for one or more disease groups, each of the one or more disease groups corresponding to a respective set of two or more ICD9 codes.

6. The computer-implemented method of claim 1, wherein:
   the user interactive controls further include one or more controls configured to enable user selection of encounter restrictions, the encounter restrictions including one or more of (i) desired demographic characteristics, (ii) desired encounter types, (iii) desired encounter date ranges, or (iv) desired patient encounter information sources; and
   the disease code distribution map includes each unique patient identifier among only the subset of the plurality of patient identifiers, the subset consisting of all patient identifiers associated with an encounter that satisfies the user-selected encounter restrictions.

7. The computer-implemented method of claim 1, wherein generating the data repository of the Hadoop cluster further includes de-identifying the patient encounter information.

8. A system for efficiently executing a population-based query of patient encounter information stored in one or more database formats, the system comprising:

a Hadoop cluster comprising a plurality of servers;
one or more processors configured to generate a data repository of the Hadoop cluster, at least in part by
  (A) extracting patient encounter information from one or more data sources that collectively store the patient encounter information in the one or more database formats, wherein the patient encounter information includes (i) information descriptive of a plurality of encounters, (ii) a plurality of patient identifiers each associated with one or more of the plurality of encounters, and (iii) a plurality of disease codes each associated with one or more of the plurality of encounters and one or more of the plurality of patient identifiers,
  (B) generating a plurality of instances of a Hadoop data model by transforming the extracted patient encounter information from the one or more database formats to a format of the Hadoop data model, wherein each instance of the Hadoop data model specifies (i) information descriptive of a single encounter of the plurality of encounters, (ii) a single patient identifier of the plurality of patient identifiers, and (iii) one or more disease codes corresponding to the single encounter and the single patient identifier, and
  (C) storing the instances of the Hadoop data model in the data repository of the Hadoop cluster; and
one or more servers that are communicatively coupled to the Hadoop cluster and configured to
  (A) provide a user at a client device with a user interface including user interactive controls, the user interactive controls including (i) one or more selection logic controls to enable selection of disease state selection logic, and (ii) an algorithm control to enable selection of either a population-based searching algorithm for applying search criteria across multiple encounters on a patient-by-patient basis, or an encounter-based searching algorithm for applying search criteria on an encounter-by-encounter basis, and
  (B) detect submission of a user query that the user entered via the user interface, wherein the user query is associated with (i) a logical expression, specified by a user setting of the one or more selection logic controls, that includes a Boolean operator operating on two or more disease states, and (ii) the population-based searching algorithm, as specified by a user setting of the algorithm control,
  (C) in response to detecting the submission of the user query, initiate a real-time query on the Hadoop cluster to identify a set of encounters that is associated with a patient cohort satisfying the logical expression on a patient-by-patient basis, irrespective of whether the patient cohort also satisfies the logical expression on an encounter-by-encounter basis, at least in part by
    accessing the data repository of the Hadoop cluster,
    generating a disease code distribution map from the instances of the Hadoop data model, wherein the disease code distribution map includes (i) each unique patient identifier among at least a subset of the plurality of patient identifiers, and (ii) for each of the unique patient identifiers, a corresponding disease code list comprising all disease codes specified by any instance of the Hadoop data model that also specifies the unique patient identifier,
    for each of the unique patient identifiers, determining whether the corresponding disease code list satisfies the logical expression, and
    for each of the unique patient identifiers having a corresponding disease code list that satisfies the logical expression, adding to the set of encounters all encounters associated with the unique patient identifier, and
  (D) provide the user an indication of at least one of (i) a number of unique patients in the patient cohort, (ii) a number of patients in the patient cohort having a particular set of one or more patient characteristics, (iii) a total number of encounters in the set of encounters associated with the patient cohort, or (iv) a number of encounters, in the set of encounters associated with the patient cohort, having one or more particular encounter characteristics.

9. The system of claim 8, wherein the plurality of disease codes comprises a plurality of International Classification of Diseases, Ninth Revision (ICD9) codes.

10. The system of claim 9, wherein the logical expression includes the Boolean operator operating on two or more ICD9 codes.

11. The system of claim 9, wherein the logical expression includes the Boolean operator operating two or more disease groups, each of the disease groups corresponding to a respective set of two or more ICD9 codes.

12. The system of claim 9, wherein the logical expression includes the Boolean operator operating on first criteria for one or more ICD9 codes and second criteria for one or more disease groups, each of the one or more disease groups corresponding to a respective set of two or more ICD9 codes.

13. The system of claim 8, wherein the one or more servers include a web server and an application node.

14. The system of claim 8, wherein:
the user interactive controls further include one or more controls configured to enable user selection of encounter restrictions, the encounter restrictions including one or more of (i) desired demographic characteristics, (ii) desired encounter types, (iii) desired encounter date ranges, or (iv) desired patient encounter information sources; and
the disease code distribution map includes each unique patient identifier among only the subset of the plurality of patient identifiers, the subset consisting of all patient identifiers associated with an encounter that satisfies the user-selected encounter restrictions.

* * * * *